United States Patent [19]

Wilde

[11] Patent Number: 5,364,875
[45] Date of Patent: Nov. 15, 1994

[54] IMIDAZOLES LINKED TO BICYCLIC HETEROCYCLIC GROUPS FOR THE TREATMENT OF ATHEROSCLEROSIS

[75] Inventor: Richard G. Wilde, New Castle, Del.

[73] Assignee: The Du Pont Merck Pharmaceutical Company, Wilmington, Del.

[21] Appl. No.: 881,033

[22] Filed: May 11, 1992

[51] Int. Cl.$^5$ .............. C07D 401/12; C07D 403/12; C07D 411/12; A61K 31/44; A61K 31/415; A61K 31/42

[52] U.S. Cl. .................................... 514/375; 514/338; 514/339; 514/340; 514/397; 546/270; 546/271; 546/273; 548/221; 548/222; 548/311.7; 548/312.1

[58] Field of Search ............ 548/343, 221, 222, 312.7, 548/311.7; 514/375, 397, 338, 339, 340; 546/270, 271, 273

[56] References Cited

U.S. PATENT DOCUMENTS

| | | | |
|---|---|---|---|
| 4,228,291 | 10/1980 | Durant et al. | 548/138 |
| 4,413,130 | 10/1983 | White | 548/340 |
| 4,460,598 | 7/1984 | Lautenschlager et al. | 514/397 |
| 4,623,662 | 11/1986 | DeVries | 514/556 |
| 4,654,358 | 3/1966 | Lautenschlager et al. | 514/398 |
| 4,722,927 | 2/1988 | Holmes | 514/256 |
| 4,824,843 | 4/1989 | Hoefle et al. | 514/228 |
| 4,868,210 | 9/1989 | Trivedi | 514/539 |
| 4,882,357 | 11/1989 | Creger et al. | 514/622 |
| 4,900,744 | 2/1990 | Billheimer et al. | 514/398 |

FOREIGN PATENT DOCUMENTS

| | | |
|---|---|---|
| 335374 | 3/1988 | European Pat. Off. . |
| 370740 | 11/1988 | European Pat. Off. . |
| 386487 | 2/1989 | European Pat. Off. . |
| 325397 | 7/1989 | European Pat. Off. . |
| 372445 | 12/1989 | European Pat. Off. . |
| 354994 | 2/1990 | European Pat. Off. . |
| 3504679 | 8/1986 | Germany . |
| 3504680 | 8/1986 | Germany . |
| 9109021 | 6/1991 | WIPO . |
| 9109030 | 6/1991 | WIPO . |
| 9110662 | 7/1991 | WIPO . |
| 9113876 | 9/1991 | WIPO . |

*Primary Examiner*—David B. Springer
*Attorney, Agent, or Firm*—Blair Q. Ferguson; Karen H. Kondrad

[57] ABSTRACT

Disclosed are imidazoles linked to bicyclic heterocyclic groups, as inhibitors of acyl-CoA:cholesterol acyltransferase (ACAT), processes for their preparation, pharmaceutical compositions, and their use as antihypercholesterolemics and/or antiatherosclerotics.

13 Claims, No Drawings

IMIDAZOLES LINKED TO BICYCLIC HETEROCYCLIC GROUPS FOR THE TREATMENT OF ATHEROSCLEROSIS

FIELD OF THE INVENTION

This invention relates to imidazoles linked to bicyclic heterocyclic groups, as inhibitors of acyl-CoA: cholesterol acyltransferase (ACAT), pharmaceutical compositions containing them, processes for their preparation, and their use as antihypercholesterolemic and/or antiatherosclerotic agents.

BACKGROUND OF THE INVENTION

Hypercholesterolemia is an established risk factor in the development of atherosclerosis. Therapeutic agents which control the level of serum cholesterol have proven to be effective in the treatment of coronary artery disease. While agents exist that can modulate circulating levels of cholesterol-carrying lipoproteins, these agents have little or no effect on the intestinal absorption of cholesterol. Dietary cholesterol can increase the level of serum cholesterol to levels which place an individual at increased risk for the development or exacerbation of atherosclerosis. Since much of the free or unesterified cholesterol that is absorbed by intestinal mucosal cells must first be esterified by ACAT prior to its incorporation and secretion into the bloodstream in large lipoprotein particles called chylomicrons, inhibition of ACAT can reduce the absorption of dietary cholesterol. In addition, the accumulation and storage of cholesteryl esters in the arterial wall is associated with increased activity of ACAT. Inhibition of the enzyme is expected to inhibit the formation or progression of atherosclerotic lesions in mammals.

There are an increasing number of patents in the literature disclosing compounds which are useful as ACAT inhibitors in particular and antiatherosclerotic agents in general. For example, U.S. Pat. No. 4,623,662, issued to DeVries on Nov. 18, 1986, discloses ureas and thioureas as ACAT inhibitors useful for reducing the cholesterol ester content of an arterial wall, inhibiting atherosclerotic lesion development, and/or treatment of mammalian hyperlipidemia. U.S. Pat. No. 4,722,927, issued to Holmes on Feb. 2, 1988, discloses disubstituted pyrimidineamides of oleic and linoleic acids as ACAT inhibitors useful for inhibiting intestinal absorption of cholesterol. U.S. Pat. No. 4,824,843, issued to Hoefle et al. on Apr. 25, 1989, and the related U.S. Pat. No. 4,882,357, issued to Creger et al. on Nov. 21, 1989, disclose a series of substituted N-phenyl-2,2-dimethyl-5-aryloxypentanamides, which prevent the intestinal absorption of cholesterol in mammals by inhibiting ACAT. European Patent Application 325,397, filed by Ito on Jul. 26, 1989, discloses a series of compounds consisting of two N-cycloalkyl-N'-arylurea units linked at nitrogen by a dialkylphenyl unit, which are inhibitors of the ACAT enzyme. U.S. Pat. No. 4,868,210, issued to Trivedi on Sep. 19, 1989, and the related European Patent Applications 335,374 filed by Trivedi on Mar. 30, 1988, and 386,487, filed by Trivedi on Feb. 9, 1989, disclose certain N-2,6-dialkyl- or N-2,6-dialkoxlphenyl-N'-arylalkyl ureas as potent inhibitors of ACAT. European Patent Application 354,994, filed by Meguro and Ikeda on Feb. 21, 1990, discloses certain N-aryl-N'-quinolin-4-yl ureas as ACAT inhibitors. European Patent Application 370,740, filed by Jackson et al. on Nov. 21, 1988, discloses ACAT inhibitors similar in composition to those of DeVries (supra).

U.S. Pat. No. 4,900,744, issued to Billheimer, et al. on Feb. 13, 1990, discloses antihypercholesterolemic thioimidazoles of the formula

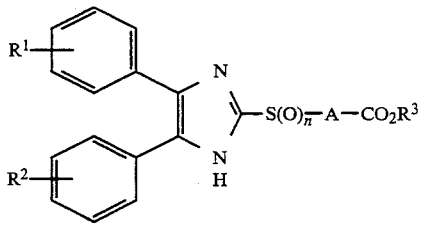

or a pharmaceutically acceptable salt thereof, wherein $R^1$ and $R^2$ independently are H, F, Cl, $CF_3$, alkyl of 1 to 4 carbon atoms, or alkoxy of 1 to 4 carbon atoms;

A is alkylene of 7-20 carbon atoms or an alkenyl residue thereof with no more than 2 double bonds;

$R^3$ is H, $CH_3$ OR $C_2H_5$; and n is 0, 1 or 2, such as 8-(4,5-diphenyl-1H-imidazol-2-ylthio)octanoic acid ethyl ester.

European Patent Application EP-A-372,445, filed by Billheimer et al. on Dec. 3, 1989, discloses compounds of formulae

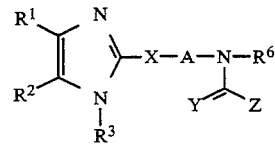

$R^1$ and $R^2$ are selected independently from H, $C_1$-$C_8$ alkyl, $C_3$-$C_8$ branched alkyl, $C_3$-$C_7$ cycloalkyl, $C_4$-$C_{10}$ cycloalkylalkyl, $C_7$-$C_{14}$ araalkyl, 2-, 3- or 4-pyridinyl, 2-thienyl, 2-furanyl, phenyl optionally substituted with 1 to 3 groups selected from F, Cl, Br, OH, $C_1$-$C_4$ alkoxy, $C_1$-$C_4$ alkyl, $C_3$-$C_8$ branched alkyl, $CH_3S(O)_r$, $NO_2$, $CF_3$, or $NR^7R^8$; or $R^1$ and $R^2$ can also be taken together as

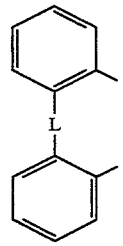

where L is O, $O(CH_2)_{m+1}O$, or $(CH_2)_m$ where m is 0–4;

$R^3$ is H, $C_1$-$C_6$ alkyl, allyl, benzyl, or phenyl optionally substituted with F, Cl, $CH_3$, $CH_3O$, or $CF_3$;

$R^4$ is straight chain $C_1$-$C_8$ alkyl optionally substituted with F; $C_3$-$C_8$ branched alkyl, $C_3$-$C_7$ cycloalkyl, $C_4$-$C_{10}$ cycloalkylalkyl, $C_7$-$C_{14}$ araalkyl where the aryl group is optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, NR⁷R⁸, or NCOR⁷; $C_3$-$C_6$ alkenyl or alkynyl, $C_1$-$C_3$ perfluoroalkyl, phenyl optionally substituted with 1 to 3 groups selected from $C_1$-$C_4$ alkyl, $C_3$-$C_8$ branched alkyl, $C_1$-$C_4$ alkoxy, F, Br, Cl, $NH_2$, OH, CN, $CO_2H$, $CF_3$, $NO_2$, $C_1$-$C_4$ carboalkoxy, $NR^7R^8$ or $NCOR^7$; pentafluorophenyl, benzyl optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, $NR^7R^8$ or $NCOR^7$; 2-, 3- or 4-pyridinyl, pyrimidinyl, or biphenyl;

$R^5$ is H, $C_1$-$C_6$ alkyl, or benzyl;

$R^6$ is $C_1$-$C_8$ alkyl, $C_3$-$C_8$ branched alkyl, $C_3$-$C_7$ cycloalkyl, $C_3$-$C_8$ alkenyl or alkynyl, phenyl optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, $NR^7R^8$ or $NCOR^7$; pentafluorophenyl, benzyl optionally substituted with 1 to 3 groups selected from $C_1$-$C_4$ alkyl or alkoxy, F, Br, Cl, $NH_2$, OH, CN, $CO_2H$, $CF_3$, $NO_2$, $C_1$-$C_4$ carboalkoxy, $NR^8R^9$ or $NCOR^7$;

$R^7$ and $R^8$ are selected independently from H or $C_1$-$C_4$ alkyl;

X is $S(O)_r$, O, $NR^5$, $CH_2$;

A is $C_2$-$C_{10}$ alkyl, $C_3$-$C_{10}$ branched alkyl, $C_3$-$C_{10}$ alkenyl, or $C_3$-$C_{10}$ alkynyl;

Y is O, S, $H_2$, NH;

Z is $NHR^4$, $OR^4$, or $R^4$;

r is 0-2, or a pharmaceutically acceptable salt thereof.

These compounds are potent in vitro inhibitors of ACAT and are therefore potential antihypercholesterolemic agents.

International Application WO 91/09021 of Bridge et al., discloses compounds of the formula:

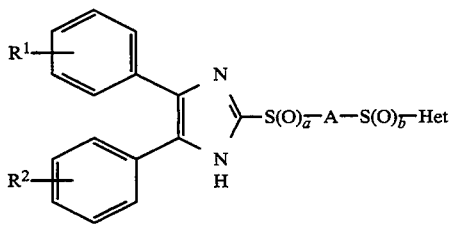

wherein

A represents methylene or a group —CH₂—A'—CH₂—, wherein

A' represents a direct bond, linear alkanediyl, alkenediyl or alkynediyl, hydroxymethylene, or optionally substituted phenylene;

$R^1$ and $R^2$ each represents hydrogen, halogen, alkyl, alkoxy, alkylthio, alkylamino, carboxy or alkoxycarbonyl;

a and b are 0, 1, or 2;

and Het represents a heterocyclic group containing from 5 to 7 ring atoms chosen from carbon, nitrogen, sulfur and oxygen atoms, and salts thereof.

These compounds are disclosed to be inhibitors of ACAT useful for the treatment of conditions such as atherosclerosis, hyperlipidemia, cholesterol ester shortage disease and atheroma in vein grafts.

International Application WO 91/10662 of Bridge et al., discloses compounds of the formula [DPIM]—S(O)-$_p$—W—Y, wherein:

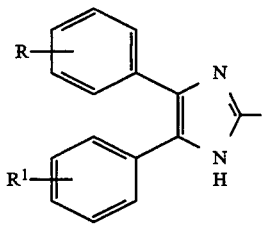

wherein R and $R^1$ each represents hydrogen, halogen, alkyl or alkoxy;

p is 0, 1, or 2;

W represents alkylene;

Y represents an optionally substituted 5- or 6-membered unsaturated ring containing 1 to 4 nitrogen atoms;

and pharmaceutically acceptable acid addition salts thereof.

Such compounds are disclosed to be inhibitors of ACAT.

International Application WO 91/13876 of Bridge et al., discloses compounds of the formula:

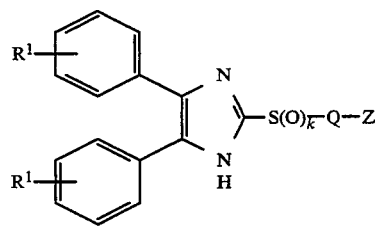

wherein $R^1$ is hydrogen or one or more substituents;

k is 0, 1, or 2;

Q is a straight or branched alkylene group;

Z is a hydrogen or a substituent group;

and pharmaceutically acceptable salts thereof.

Such compounds are disclosed to be inhibitors of ACAT.

U.S. Pat. No. 4,460,598, issued to Lautenschläger et al. on Jul. 17, 1984, discloses compounds of the formula:

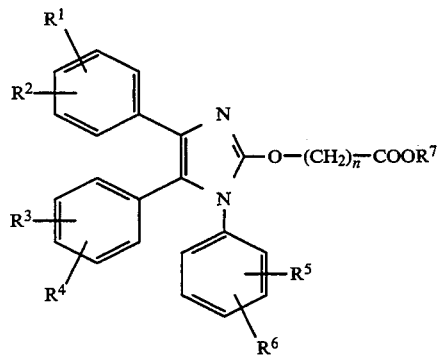

wherein $R^1$, $R^2$, $R^3$, $R^4$, $R^5$ and $R^6$ independently are H, F, Cl, Br, I, alkyl, alkoxy, or $CF_3$, with the proviso that one or several of $R^1$ and $R^2$, $R^3$ and $R^4$, or $R^5$ and $R^6$ taken together represent methylenedioxy;

$R^7$ is H, alkali metal ion, alkyl of 1 to 6 carbon atoms, or benzyl; and n is 0 to 10.

The synthesis and the use of these compounds in the treatment of thromboembolic, inflammatory and/or atherosclerotic diseases is disclosed.

U.S. Pat. No. 4,654,358, issued to Lautenschläger et al. on Mar. 31, 1987, discloses compounds of the formula:

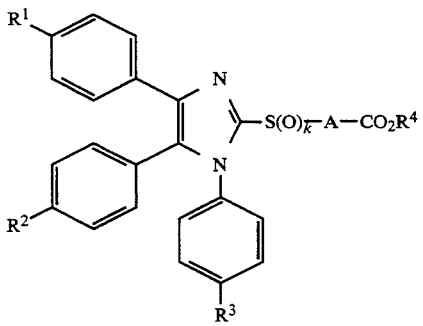

wherein k is 0, 1, or 2, $R^1$, $R^2$ and $R^3$ independently are H, F, Cl, $CH_3$, $CH_3O$, or $CF_3$;

$R^4$ is H, Na, K, $CH_3$, $CH_3CH_2$, $(CH_3)_2CH$, $CH_3(CH_2)_2$, or butyl;

A is $C(CH_3)_2$, $CH(CH_2)_mCH_3$, $(CH_2)_n$, or $(CH_2)_{n-2}CH(CH_3)$;

m is 0 to 8; and n is 2 to 10.

The synthesis and the use of these compounds in the treatment of inflammatory diseases, diseases of lipid metabolism, and/or hyperlipidemic diseases is disclosed.

German Laid Open Application No. DE 3504679, Lautenschläger et al., published Aug. 14, 1986, discloses compounds of the formula:

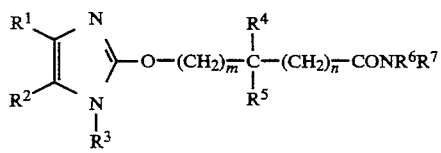

wherein $R^1$, $R^2$ and $R^3$ independently are H, alkyl of 1 to 6 carbon atoms, cycloalkyl of 1 to 6 carbon atoms, or

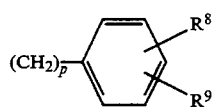

$R^4$ and $R^5$ independently are H, $C_6H_5$, or alkyl of 1 to 9 carbon atoms;

$R^6$ and $R^7$ independently are H, OH, saturated or unsaturated alkyl, cycloalkyl, or hydroxyalkyl of 1 to 10 carbon atoms,

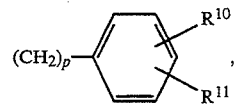

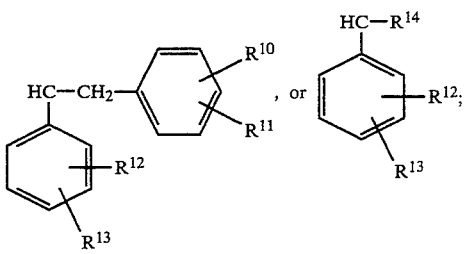

$R^8$, $R^9$, $R^{10}$, $R^{11}$, $R^{12}$ and $R^{13}$ independently are H, F, Cl, Br, $NO_2$, $CH_3CONH$, OH, alkyl of 1 to 3 carbon atoms, $CF_3$, and alkoxy of 1 to 3 carbon atoms, with the proviso that $R^8$ and $R^9$, $R^{10}$ and $R^{11}$, or $R^{12}$ and $R^{13}$ taken together represent methylenedioxy;

$R^{14}$ is alkyl of 1 to 2 carbon atoms;

m and n taken together represent a whole number from 0 to 9;

p is 0 to 2;

s is 0 to 2; and t is 0 or 2.

The synthesis and the use of these compounds in the treatment of thromboembolic, inflammatory, atherosclerotic, and lipid metabolism diseases in general is disclosed.

German Laid Open Application No. DE 3504680, Lautenschläger et al., published Aug. 14, 1986, discloses compounds of the formula:

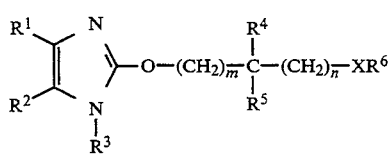

wherein $R^1$, $R^2$ and $R^3$ independently are H, alkyl of 1 to 6 carbon atoms, cycloalkyl of 1 to 6 carbon atoms, or

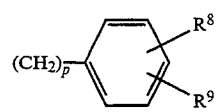

$R^1$ and $R^2$ can be taken together with the carbon atoms in the 4 and 5 position of the imidazole ring to represent a carbocyclic five- or six-membered aromatic or partially hydrogenated ring which may be substituted by $R^8$ or $R^9$;

$R^4$ and $R^5$ independently are H, $C_6H_5$, or alkyl of 1 to 9 carbon atoms;

$R^6$ is alkyl, cycloalkyl, or hydroxyalkyl of 1 to 20 carbon atoms, H, alkali metal if X is —COO—, 1-phenethyl, or

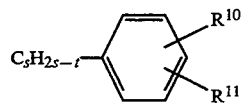

$R^7$ is H, OH if X is —CONR$^7$—, or alkyl of 1 to 4 carbon atoms;

$R^8$, $R^9$, $R^{10}$ and $R^{11}$ are independently H, Cl, F, Br, NO$_2$, CH$_3$CONH, OH, alkyl of 1 to 3 carbon atoms, CF$_3$, or alkoxy of 1 to 3 carbons, or $R^8$ and $R^9$ or $R^{10}$ and $R^{11}$ taken together represent methylene-dioxy;

X is a bond, O, OC(=O)O, C(=O)O, CONR$^7$, OC(=O), or OC(=O)NR$^7$;

m and n taken together represent a whole number from 0 to 9;

p is 0 to 2;

s is 0 to 2; and t is 0 or 2.

The synthesis and the use of these compounds in the treatment of thromboembolic, inflammatory, atherosclerotic, and lipid metabolism diseases in general is disclosed.

Durant et al., U.S. Pat. 4,228,291, issued Oct. 14, 1980, teaches compounds of the formula:

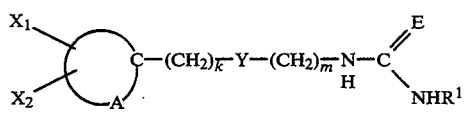

wherein:

A together with the carbon atom form an unsaturated heterocyclic nucleus which may be an imidazole, pyrazole, pyrimidine, pyrazine, pyridazine, thiazole, isothiazole, oxazole, isoxazole, triazole, thiadiazole, benzimidazole, or 5,6,7,8-tetrahydroimidazol[1,5-a]pyridine ring;

X$_1$ is H, lower alkyl, hydroxyl, trifluoromethyl, benzyl, halogen, amino, or

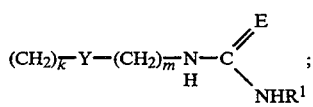

X$_2$ is H, or when X$_1$ is lower alkyl, lower alkyl or halogen;

k is 0 to 2 and m is 2 or 3, provided that the sum of k and m is 3 or 4;

Y is O, S, or NH;

E is NR$^2$;

R$^1$ is H, lower alkyl or di-lower alkyl amino-lower alkyl;

and R$^2$ is H, nitro, or cyano.

The compounds are said to be antihistamines of the H$_2$ receptor blocking type, as well as having anti-inflammatory activity.

White, U.S. Pat. 4,413,130, Nov. 1, 1983, discloses histamine H$_2$ receptor antagonists of the formula:

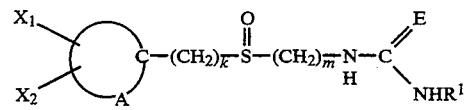

wherein

A together with the carbon atom form an unsaturated heterocyclic nucleus which may be an imidazole, pyridine, thiazole, isothiazole, oxazole, isoxazole, pyrazole, triazole, thiadiazole, pyrimidine, pyrazine or pyridazine;

X$_1$ and X$_2$ may be H, lower alkyl, trifluoromethyl, hydroxyl, halogen, amino, or X$_1$ and X$_2$ and at least two of the atoms comprising A may form a further ring;

k is 0 to 2 and m is 2 or 3, provided that the sum of k and m is 3 or 4;

E is O, S, or NR$^2$;

R$^1$ is H, lower alkyl, acyl, or dialkylamino-alkyl;

and R$^2$ is H, NO$_2$, CN, alkansulphonyl or arenesulphonyl.

There are no known literature references disclosing the imidazoles of this invention, their use as ACAT inhibitors, or their use to lower cholesterol or in the treatment of atherosclerosis.

DETAILED DESCRIPTION OF THE INVENTION

The present invention provides novel compounds of Formula (I), processes for their preparation, pharmaceutical compositions containing such heterocyclic compounds, and therapeutic methods for their use as antihypercholesterolemic and/or antiatherosclerotic agents.

This invention provides compounds of Formula (I):

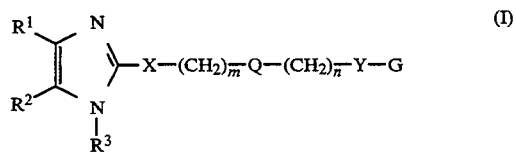

and stereoisomers and pharmaceutically acceptable salts thereof wherein:

X and Y are selected independently from the groups S(O)$_p$, CH$_2$, or NR$^4$;

Q is selected from either CH$_2$, or an aromatic ring selected from the group consisting of benzene, pyridine, pyrrole, furan, or thiophene, said aromatic ring being connected through two ring substitution sites and said aromatic ring being optionally substituted with 1-3 groups independently selected from F, Cl, Br, OH, C$_1$-C$_4$ alkoxy, C$_1$-C$_4$ alkyl, C$_3$-C$_8$ branched alkyl, S(O)$_t$(C$_1$-C$_6$ alkyl), NO$_2$, CF$_3$, or NR$^{15}$R$^{16}$;

G is a bi- or tri-cyclic aromatic heterocyclic group, composed of five- and six-membered rings, containing at least one nitrogen atom, and being optionally substituted at valence-allowed sites with 1-3 groups independently selected from F, Cl, Br, OH, C$_1$-C$_4$ alkoxy, C$_1$-C$_4$ alkyl, C$_3$-C$_8$ branched alkyl, S(O)$_t$(C$_1$-C$_6$ alkyl), NO$_2$, CF$_3$, or NR$^{15}$R$^{16}$;

R$^1$ and R$^2$ are selected independently from H, C$_1$-C$_8$ alkyl, C$_3$-C$_8$ branched alkyl, C$_3$-C$_7$ cycloalkyl, C$_4$-C$_{10}$ cycloalkylalkyl, C$_7$-C$_{14}$ aralkyl, pyridyl, thienyl, furanyl, or phenyl; each being optionally substituted with 1-3 groups independently selected from F, Cl, Br, OH, $C_1$–$C_4$ alkoxy, $C_1$–$C_4$ alkyl, $C_3$–$C_8$ branched alkyl, $S(O)_t(C_1$–$C_6$ alkyl), $NO_2$, $CF_3$, or $NR^{15}R^{16}$;

$R^3$ is H, $C_1$–$C_6$ alkyl, allyl, benzyl, or phenyl; each being optionally substituted with F, Cl, $CH_3$, $OCH_3$, or $CF_3$;

$R^4$ is H, $C_1$–$C_8$ alkyl, $C_3$–$C_{10}$ alkoxyalkyl, $C_5$–$C_{12}$ (alkoxy)alkoxy-alkyl, $C_3$–$C_8$ branched alkyl, $C_7$–$C_{14}$ phenylalkyl, or phenyl, each being optionally substituted with 1-3 groups selected from $C_1$–$C_4$ alkyl, $C_1$–$C_4$ alkoxy, $C_2$–$C_8$ dialkylamino, $C_1$–$C_4$ alkylthio, halogen, or $NO_2$;

$R^{15}$ and $R^{16}$ are selected independently from H, $C_1$–$C_8$ alkyl, benzyl, or phenyl;

m and n are independently 0–6, and selected so that the total number of $CH_2$ groups in the chain between X and G is at least 2; and p and t are independently 0–2.

Preferred are compounds of Formula (I), wherein
X and Y are independently $S(O)_p$ or $NR^4$;

Q is selected from either $CH_2$, or an aromatic ring selected from the group consisting of benzene, pyridine, pyrrole, furan or thiophene, said aromatic ring being connected through two ring substitution sites and said aromatic ring being optionally substituted with a 1-3 groups independently selected from $C_1$–$C_4$ alkyl, $C_1$–$C_4$ alkoxy, $C_2$–$C_8$ dialkylamino, $C_1$–$C_4$ alkylthio, halogen or $NO_2$;

G is selected from the groups

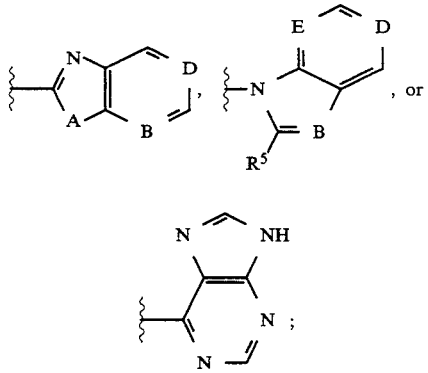

each being optionally substituted at valence-allowed sites with 1-3 groups independently selected from $C_1$–$C_4$ alkyl, $C_1$–$C_4$ alkoxy, $C_2$–$C_8$ dialkylamino, $C_1$–$C_4$ alkylthio, halogen, or $NO_2$;

wherein A is O S or NH, and B, D and E are independently CH or N;

$R^1$ and $R^2$ are selected independently from H, $C_1$–$C_4$ alkyl, $C_3$–$C_8$ branched alkyl, $C_3$–$C_7$ cycloalkyl, or phenyl, each being optionally substituted with 1-3 groups selected from Cl, $C_1$–$C_4$ alkyl, $C_1$–$C_4$ alkoxy, $C_2$–$C_8$ dialkylamino, or $C_1$–$C_4$ alkylthio;

$R^3$ is H;

$R^4$ is H, $C_1$–$C_8$ alkyl, $C_3$–$C_{10}$ alkoxyalkyl, $C_5$–$C_{12}$ (alkoxy)alkoxy-alkyl, $C_3$–$C_8$ branched alkyl, $C_7$–$C_{14}$ phenylalkyl, or phenyl, each being optionally substituted with 1-3 groups selected from $C_1$–$C_4$ alkyl, $C_1$–$C_4$ alkoxy, $C_2$–$C_8$ dialkylamino, $C_1$–$C_4$ alkylthio, halogen, or $NO_2$;

m and n are independently 0–6, and selected so that the total number of $CH_2$ groups in the chain between X and G is at least 2; and p is 0–2;

$R^5$ is H, $C_1$–$C_4$ alkyl, $C_3$–$C_7$ branched alkyl, $C_1$–$C_4$ alkoxy, $C_1$–$C_4$ alkylthio, or $NR^6R^7$;

$R^6$ and $R^7$ are independently selected from the groups H, $C_1$–$C_4$ alkyl, or phenyl.

More preferred because of their biological activity are compounds of Formula (I), wherein:

X and Y are independently $S(O)_p$ or $NR^4$;

Q is selected from either $CH_2$, benzene, furan or thiophene, wherein the benzene, furan, or thiophene are unsubstituted except for the connection through two ring substitution sites;

G is selected from the groups

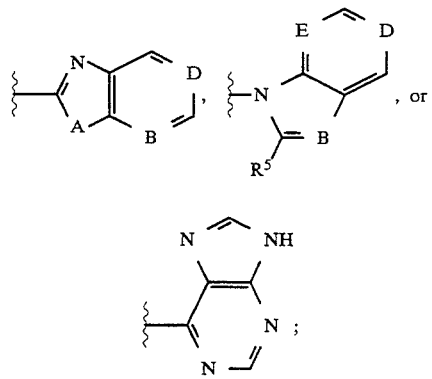

each being optionally substituted at valence-allowed sites with 1-3 groups independently selected from $C_1$–$C_4$ alkyl, $C_1$–$C_4$ alkoxy, $C_2$–$C_8$ dialkylamino, $C_1$–$C_4$ alkylthio, halogen or $NO_2$;

wherein A is O, S or NH; and B, D and E are independently CH or N;

$R^1$ and $R^2$ are selected independently from $C_3$–$C_8$ branched alkyl, $C_3$–$C_7$ cycloalkyl, or phenyl, phenyl being optionally substituted with one of $CH_3O$, $(CH_3)_2N$, or $CH_3S$;

$R^3$ is H;

$R^4$ is $C_1$–$C_8$ alkyl, $C_3$–$C_{10}$ alkoxyalkyl, $C_5$–$C_{12}$ (alkoxy)alkoxyalkyl, $C_3$–$C_8$ branched alkyl, or phenyl;

m is 1–3;

n is 0–3;

p is 0;

$R^5$ is H, $C_1$–$C_4$ alkyl, $C_3$–$C_7$ branched alkyl, $C_1$–$C_4$ alkoxy, $C_1$–$C_4$ alkylthio, or $NR^6R^7$;

$R^6$ and $R^7$ are independently selected from the groups H, $C_1$–$C_4$ alkyl, or phenyl.

Representative compounds of the invention include:

2-[5-(N-(1H-benzoxazol-2-yl)-N-heptylamino)pentyl]thio-4,5-diphenyl-1H-imidazole;

4,5-bis(4-methoxyphenyl)-2-[5-(N-(1H-benzoxazol-2-yl)-N-heptylamino)-pentyl]thio-1H-imidazole;

4,5-bis(4-methoxyphenyl)-2-[5-(N-(1H-benzimidazol-2-yl)-N-heptylamino)-pentyl]thio-1H-imidazole;

4,5-bis(4-dimethylaminophenyl)-2-[5-(2-(1-methylethyl)-1H-benzimidazol-1-yl)pentyl]thio-1H-imidazole.

The compounds described above are useful as antiatherosclerotic and antihypercholesterolemic agents in a mammal when administered as pharmaceutical compositions to a mammal in need of treatment with such antiatherosclerotic and antihypercholesterolemic agents. The present invention includes pharmaceutical compositions containing an effective ACAT-inhibiting or antiatherosclerotic amount of the above described compounds of Formula I. The present invention also includes methods of treating hypercholesterolemia or atherosclerosis in a mammal comprising administering to the mammal a therapeutically effective amount of a compound of Formula I described above.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention.

When any variable (for example, $R^1$ through $R^{21}$) occurs more than one time in any constituent or structure herein, its definition on each occurrence is independent of its definition at every other occurrence. Also, combinations of substituents and/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl and cyclooctyl; and "biycloalkyl" is intended to include saturated bicyclic ring groups such as [3.3.0] bicyclooctane, [4.3.0] bicyclononane, [4.4.0] bicyclodecane (decalin), [2.2.2] bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like. "Halo" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; "carbocyclic" is intended to mean any stable 5- to 7- membered monocyclic or bicyclic or 7- to 14-membered bicyclic or tricyclic carbon ring, any of which may be saturated, partially unsaturated, or aromatic, for example, indanyl or tetrahydronaphthyl (tetralin).

As used herein, the term "heterocycle" is intended to mean a stable 5- to 7- membered monocyclic or bicyclic or 7- to 10-membered bicyclic heterocyclic ring which is either saturated or unsaturated, and which consists of carbon atoms and from 1 to 3 heteroatoms selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl. The term "substituted", as used herein, means that an one or more hydrogen on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious therapeutic agent.

As used herein, "pharmaceutically acceptable salts and prodrugs" refer to derivatives of the disclosed compounds that are modified by making acid or base salts, or by modifying functional groups present in the compounds in such a way that the modifications are cleaved, either in routine manipulation or in vivo, to the parent compounds. Examples include, but are not limited to, mineral or organic acid salts of basic residues such as amines; alkali or organic salts of acidic residues such as carboxylic acids; acetate, formate and benzoate derivatives of alcohols and amines; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

SYNTHESIS

The novel compounds of Formula (I) may be prepared using the reactions and techniques described in this section. The reactions are performed in solvents appropriate to the reagents and materials employed and are suitable for the transformations being effected. Also, in the description of the synthetic methods provided below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the educt molecule must be compatible with the reagents and reactions proposed. Not all compounds of Formula (I) falling into a given class may be compatible with some of the reaction conditions required in some of the methods described. Such restrictions to the substituents which are compatible with the reaction conditions will be readily apparent to one skilled in the art and alternate methods must then be used.

The strategy of synthesis of compounds of Formula I can be chosen based on the availability of starting materials. One must chose such a strategy from among two cases, which are shown in Scheme I. The first is to begin with a compound such as compound 1, wherein J represents a group susceptible to displacement by nucleophilic reagents, such as halide, alkanesulfonate, arylsulfonate, and the like, and M represents a different group which is not susceptible to nucleophilic attack but is suitable for manipulation (by oxidation, deprotection, functionalization, or other transformations familiar to the organic chemist)to give such a leaving group in a later step. The second case is to begin with a compound such as compound 7, a dielectrophile.

In the former case, either the imidazole group or the G group is introduced first in the synthesis by nucleophilic coupling to give either compound 2 or 5. This general type of alkylative coupling reaction will be referred to throughout this section, and will be discussed in greater detail below. The M group is then transformed to a J leaving group, and the other heterocyclic group is coupled in a third step. In the latter case, the least reactive heterocycle (only 1 molar equivalent or less) is coupled to compound 7 to give either compound 3 or 6, which are used to prepare the final product. This second case is one step fewer than the first, although the possibility exists for the coupling of two units of the chosen heterocyclic reagent with compound 7. The laws of statistics give this result as being 25% probable. This by-product may be minimized by proper choice of the heterocycle, the J group, stoichiometry, and choice of the reaction conditions. For example, choosing J=Cl or a similarly-mild leaving group and using excess quantities of reagent 7 can give good yields of compounds 3 or 6.

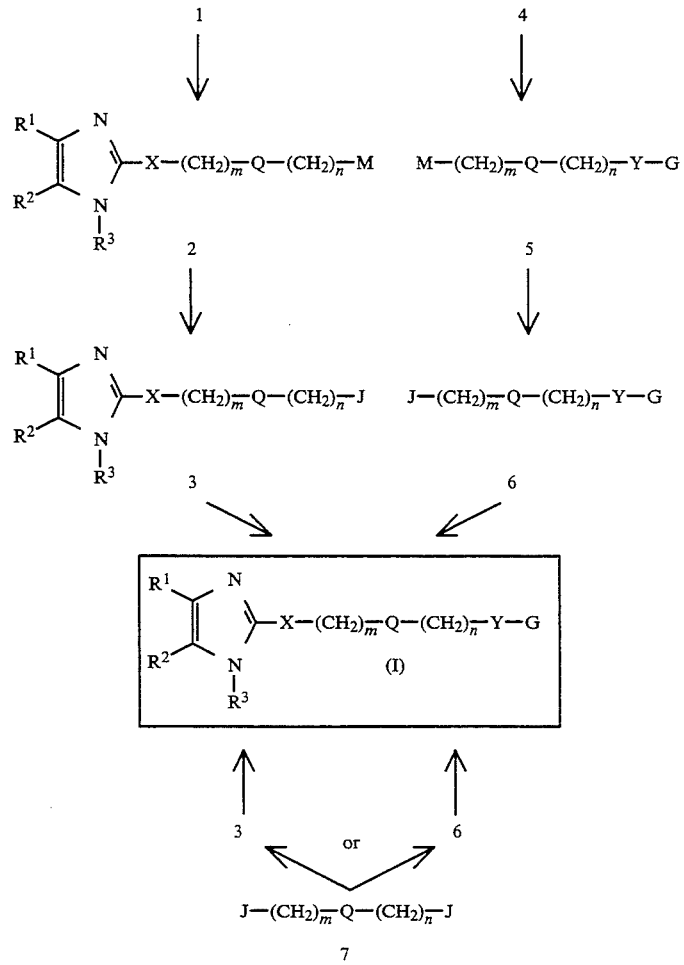

The source of compounds such as 1, 4, or 7 will depend upon the choice of the Q group and the values for m and n. For example, for $Q=CH_2$, two examples of differentiated functionalized compounds could be whalo esters (such as compound 8 in Scheme II) or bromochloroalkanes (compound 16, Scheme III). In the haloester scheme, the first step of the sequence involves displacement of a bromide ion by a suitably-nucleophilic form of either the imidazole or the G group (see below). The ester group in compounds such as 9 or 13 can be transformed to a hydroxymethylene group by the use of such reagents as lithium aluminum hydride or diisobutylaluminum hydride. The hydroxyl group in compounds 10 and 12 can be transformed to a halide or other leaving group by standard methods (bromide is arbitrarily shown for compounds 11 and 15). Alcohols can be converted to chlorides by many reagents, including triphenylphosphine in carbon tetrachloride or hexachloro-ethylene, thionyl chloride or phosphorus oxychloride. Conversion to bromides is achieved by such reagents as phosphorus tribromide, carbon tetrabromide/triphenylphosphine or thionyl bromide. Iodides are prepared from alcohols by such reagents as triphenylphosphine/iodine or iodotrimethylsilane. Alcohols can be converted to the toluenesolfonate leaving group by the action of toluenesulfonyl chloride and an amine base such as pyridine. Alcohols can be converted to alkanesulfonate leaving groups by the action of either the corresponding sulfonyl anhydride or chloride and an amine base such as triethylamine. The bromide of compounds 11 or 15 can be displaced in the standard way to give compound 12, the final product.

Similarly, Scheme III shows how a bromochloroalkane (compound 16) may also be used as a differentiated dielectrophile. Alkylation of compound 16 occurs selectively mono, with bromide displacement, to give either compound 17 or 18. The second displacement reaction may then be allowed to occur under more forceful conditions (see below) to afford the product, compound 12.

tion provided by such reagents as benzoyl peroxide, azoisobutyonitrile or UV light effect the bromination of a benzyl group to give an a-bromomethylene group in compound 20. Displacement and introduction of the imidazole system gives compound 21. Reduction of the carboxylic ester group as discussed above gives the alcohol compound 22, and transformation to a leaving group as discussed above gives the compound 23. Displacement of the J group then yields the final product, compound 24.

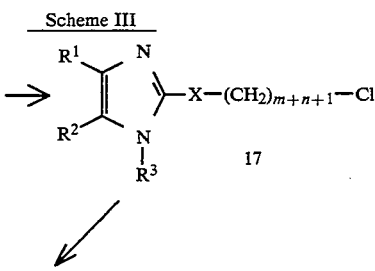

Scheme III

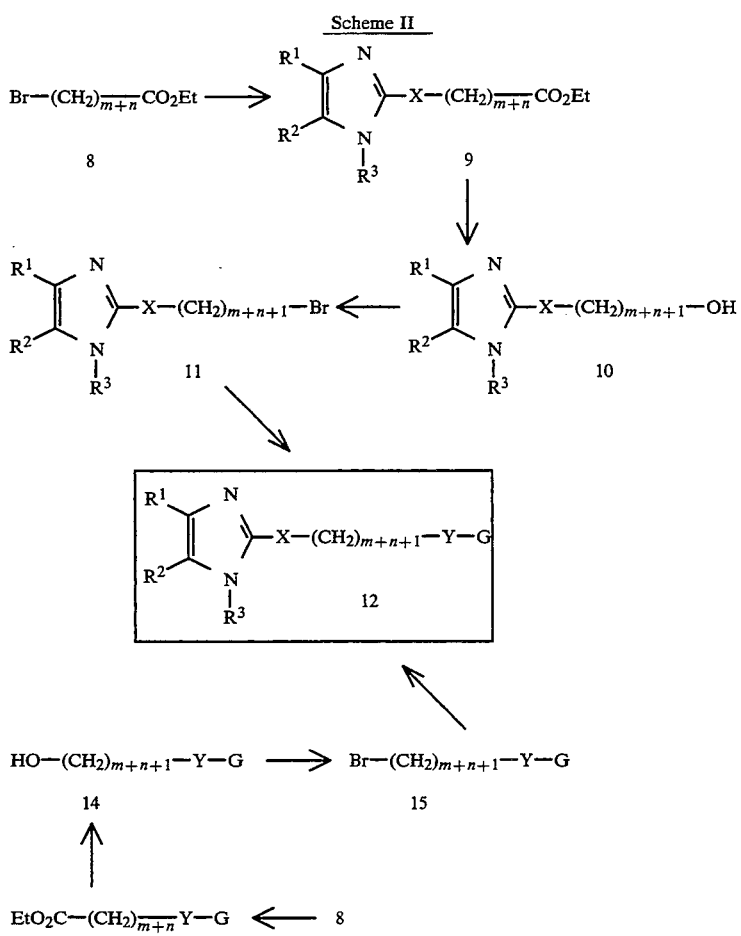

Scheme II

Much of the same technology presented in Schemes I, II, and III may be employed for compounds wherein Q is chosen to be an aromatic ring (either phenylene or a heterocycle). Synthesis of the starting materials for these routes would also largely depend upon the available starting material. One method, used for when either n or m=1, involves the free-radical bromination of a methyl group on the ring of an aralkanoate ester (compound 19, Scheme IV). Treatment with such reagents as N-bromosuccinimide, N-bromophthalimide, or 1,3-dibromo-5,5-dimethylhydantoin with free-radical initia- -continued
Scheme III

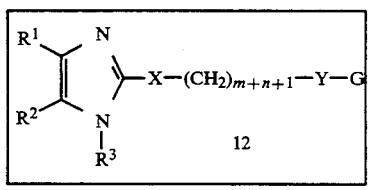

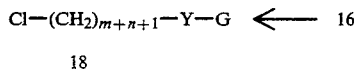

For a general Q group, the technology required to extend a chain to prepare any length of m or n can begin with the Q group bearing a carboxylic ester group. This chain-extension methodology should be readily familiar to those skilled in the art, and only a few of the many possible routes to achieve this goal will be discussed here. Scheme V shows a plan for making alcohols with chains of 1, 2, 3, and n methylene units long, starting with carboxylic ester 25. Reagents such as lithium aluminum hydride will reduce the ester group to a hydroxy-methylene group (compound 26), which can be oxidized to the aldehyde 27 by such reagents as dimethylsulfoxide/oxalyl chloride/triethylamine. Alternatively, the carboxylic ester may be directly reduced to an aldehyde group with bulky reducing agents such as diisobutylaluminum hydride at low temperature. Aldehyde-bearing compound 27 may be allowed to undergo reaction with such reagents as triphenylphosphonium methylide to give vinyl compound 28. Hydroxylation of the vinyl group may be achieved by using such reagents as 9-BBN followed by basic hydrogen peroxide, to afford the hydroxyethyl compound 29. The reaction of the aldehyde 27 with a reagent such as the anion of a diethyl alkoxycarbonylmethylphosphonate would produce the unsaturated ester group of compound 30. Both the carbon-carbon double bond and the alkoxycarbonyl group may be reduced using such reagents as lithium/ liquid ammonia, thus generating the hydroxypropyl compound 31. Finally, an extension to a chain of length n may be achieved by the reaction of aldehyde compound 27 with a (siloxy)alkylidene triphenyl-phosphorane reagent. The double bond in compound 32 may be reduced using hydrogen and palladium, platinum or other catalysts. Removal of the silicon group may be achieved by the use of such reagents as tetrabutylammonium fluoride.

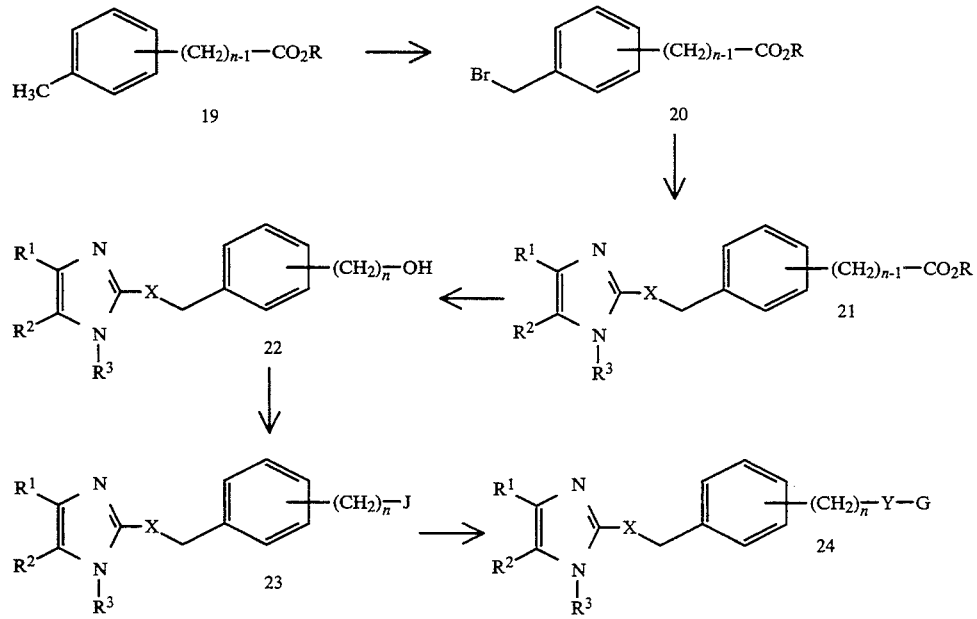

Scheme IV

The coupling of an intermediate bearing the Q group (compound 35 or 37 in Scheme VI) by displacement of a leaving group is accomplished by a nucleophilic reagent introducing either heterocycle (compound 34 or 38). The conditions of the reaction will depend upon the choice of X or Y; for X or Y=S or NH, the reaction is performed under basic conditions, in the presence of an inorganic reagent such as potassium carbonate, in polar aprotic solvents such as dimethylformamide or tetrahydrofuran at elevated temperatures. A catalyst may be used to facilitate the reaction, such as tetrabutylammonium iodide. Alternatively, the salts of compounds 34 or 38 may be prepared by the treatment with such a reagent as sodium hydride. The salt, prepared in situ, is then allowed to react with the electrophiles 35 or 37 to give the coupled products (compounds 36 or 39).

Scheme V

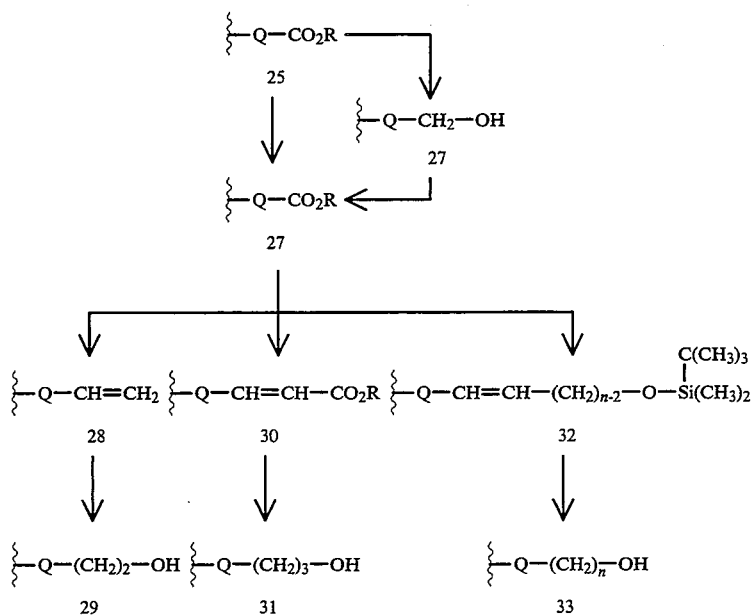

In the case where X is CH$_2$, a convenient coupling reaction is shown in Scheme VII. A 2-unsubstituted imidazole is protected at nitrogen with an ethoxyethyl group (compound 40), prepared by the action of ethyl vinyl ether and an acid catalyst. Compound 40 can be deprotonated selectively at the 2-position using a strong base such as n-butyllithium. The anion (intermediate 41) is then allowed to react with electrophile 35 to generate the coupled product, compound 42. The ethoxyethyl protecting group may be removed at a later point, and the R$^3$ group may then be introduced.

Scheme VI

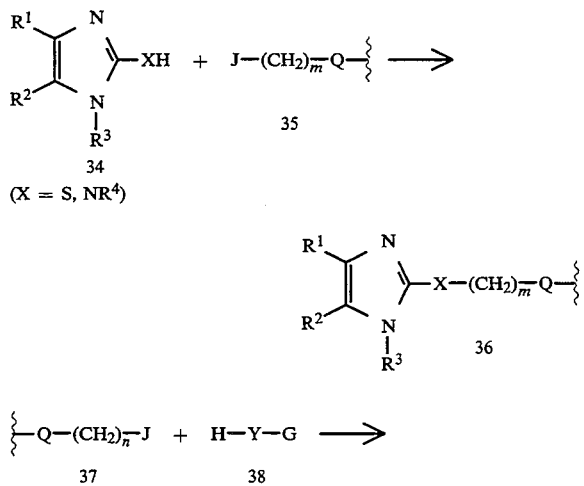

Scheme VII

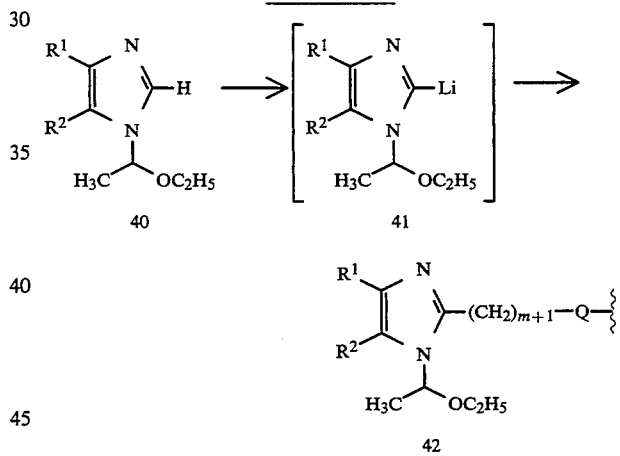

When Y is NR$^4$, a special synthesis may be used involving a nucleophilic aromatic displacement reaction (Scheme VIII). For this purpose, the compound containing the NR$^4$ group is required (compound 46). This can be prepared, starting with ester-bearing compound 43 (prepared using technology discussed above). The ester may be cleaved to the carboxylic acid (compound 44), using such reagents as sodium hydroxide in aqueous ethanol or lithium iodide in warm dimethyl-sulfoxide. The acid may then be coupled to an amine to give the amide compound 45. This reaction may be performed with such reagents as dicyclohexylcarbodiimide and catalysts such as 1-hydroxy-1H-benzotriazole. The amide carbonyl group may then be reduced to a methylene, using such reagents as lithium aluminum hydride or boranetetrahydrofuran complex. The amine, compound 46, is then used to displace a leaving group (J) from a heterocyclic compound such as 47 or 49. Particularly successful choices for J include Cl and SO$_2$CH$_3$. The reaction proceeds in the presence of a base such as diisopropylethyl-amine, in a polar aprotic solvent such as acetonitrile at reflux temperature. Application of high pressure to the reaction vessel (1000–5000 psi) may also be used to accelerate the process.
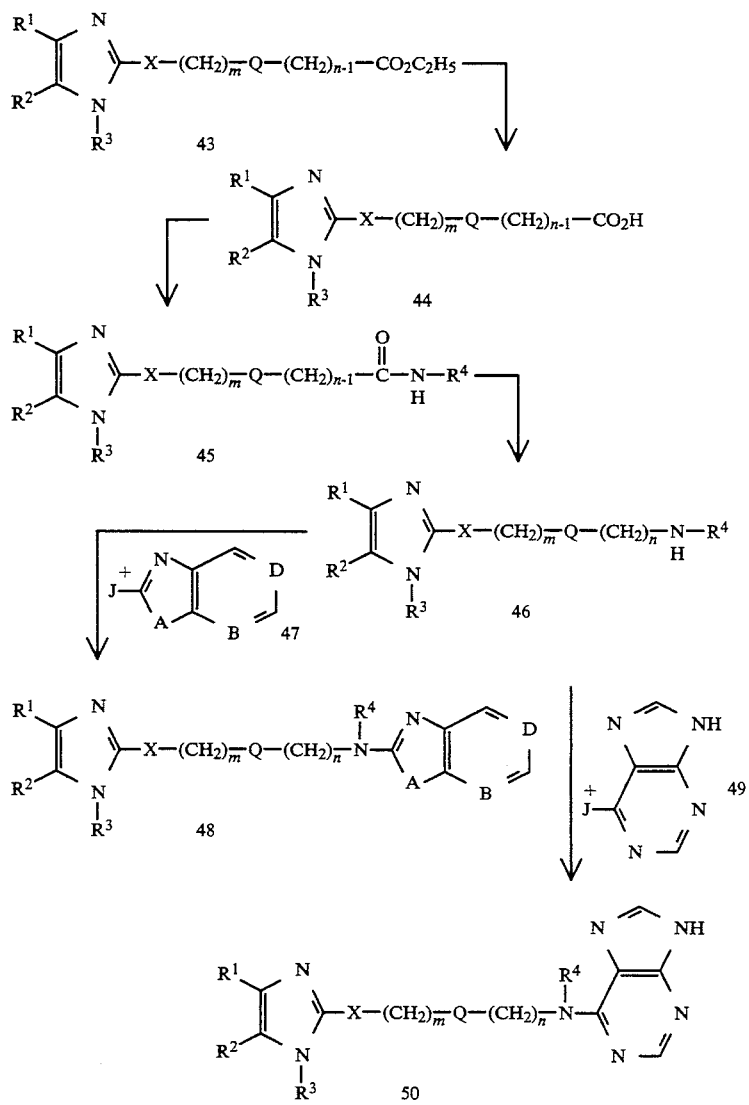
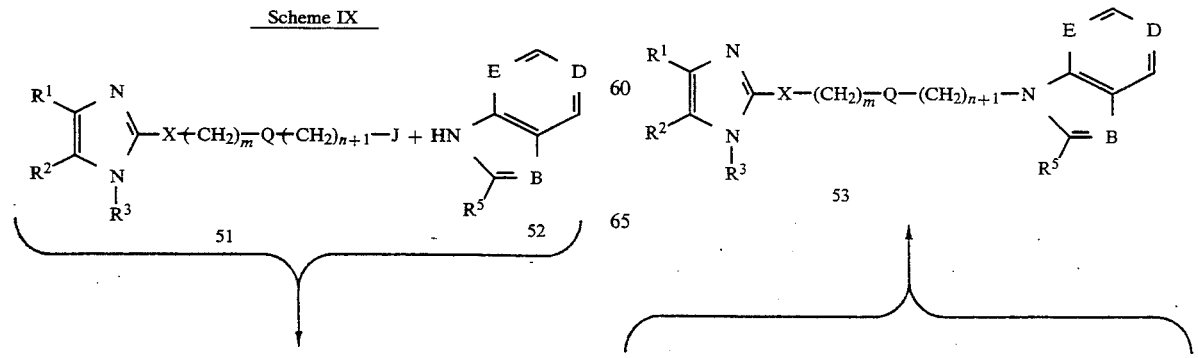

-continued
Scheme IX

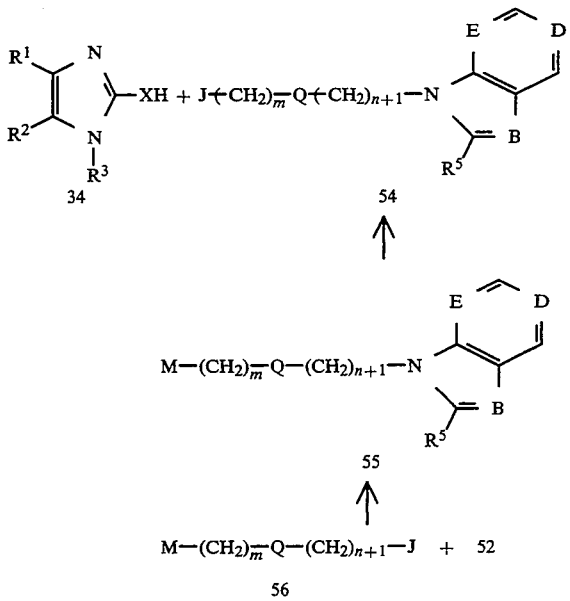

The synthesis of compounds with the G group attached to the rest of the molecule at a ring nitrogen atom is shown in Scheme IX. Such a bond may be formed by alkylation of the nitrogen atom with a J-bearing intermediate, either compound 51 (which already bears the imidazole group), or a simpler electrophile (compound 56), which requires two more steps (55 to 54 to 53) to generate the desired final product.

All the heterocyclic starting materials employed in this section can be easily prepared by well-established protocols in heterocyclic chemistry. Such protocols are well-covered in the common literature, and are readily apparent to those skilled in the art.

In the cases where X or Y is SO or $SO_2$, the corresponding sulfides may be oxidized to their sulfoxide or sulfone counterparts by the use of such reagents as m-chloroperbenzoic acid, potassium peroxomonosulfate, potassium permanganate, and the like. Control of the extent of the oxidation may be achieved by control of stoichiometry, temperature and/or solvent.

The compounds of this invention and their preparation can be further understood by the following examples, which exemplify but do not constitute a limit of the invention. In these examples, unless otherwise indicated, all temperatures are in degrees centigrade and parts and percentages are by weight.

EXAMPLE 2

Preparation of 4,5-bis(4-methoxyphenyl)-2-[5-(1H-benzimidazol-2-yl)pentyl]thio-1H-imidazole Part A. A solution of 2-mercapto-1H-benzimidazole (4.75 g, 31.6 mmol), ethyl 5-bromovalerate (5.00 mL, 31.6 mmol), potassium carbonate (5.68 g, 41.1 mmol), and tetra-n-butylammonium iodide (2.33 g, 6.31 mmol) in tetrahydrofuran (200 mL) was heated to reflux for 24 hours. The solution was cooled, and poured into water (200 mL). The layers were separated, and the aqueous layer was extracted with methylene chloride (2×200 mL). All three organic phases were washed over brine, combined, dried over anhydrous magnesium sulfate, filtered and evaporated to afford a pale yellow oil. The oil was purified by elution through a short plug of silica gel (1:1 ethyl acetate-hexane) to afford the product, 2-[4-(carboethoxy)butylthio]-1H-benzimidazole, as a waxy solid, m.p. 88°–90° C. (8.03 g, 28.9 mmol, 91%). $^1H$ NMR ($CDCl_3$): 10.61 (1H, br s); 7.66 (1H, br s); 7.36 (1H, br s); 7.19 (2H, dd, J=5.7, 2.7 Hz); 4.12 (2H, q, J=7.0 Hz); 3.30 (2H, t, J=6.2 Hz); 2.32 (2H, t, J=5.9 Hz); 1.95–1.74 (4H, m); 1.24 (3H, t, J=7.0 Hz).

Part B. A solution of the ester prepared in Part A above (5.62 g, 20.2 mmol)in tetrahydrofuran (50 mL) was added dropwise to a solution of sodium bis(methoxyethoxy)aluminum hydride (15.0 mL of commercial 3.4M solution in toluene, 51.0 mmol) in tetrahydrofuran (50 mL) at 0° C. The ice bath was removed, and the solution was stirred at room temperature for 24 hours. The mixture was cooled back to 0° C., and the excess reagent was quenched by the careful addition of aqueous sodium hydroxide solution (10 mL of 2N). The mixture was partitioned between water and methylene chloride, and the organic layer was dried over anhydrous magnesium sulfate, filtered and evaporated. The residual oil was sufficiently pure product, 2-(5-hydroxypentyl)thio-1H-benzimidazole (4.50 g, 19.0 mmol, 94%), which was used directly in the next step. $^1H$ NMR ($CDCl_3$): 7.49 (2H, br s); 7.21–7.15 (2H, m); 3.63 (2H, t, J=5.9 Hz); 3.29 (2H, t, J=7.3 Hz); 1.84–1.70 (2H, m); 1.61–1.43 (4H, m).

Part C. A solution of the alcohol prepared in Part B above (4.50 g, 19.0 mmol) and carbon tetrabromide (15.1 g, 45.5 mmol) in methylene chloride (60 mL) was cooled to 0° C., and a solution of triphenylphosphine (11.6 g, 44.4 mmol) in methylene chloride (50 mL) was added dropwise. After stirring for 18 hours, the solution was evaporated, and the residual oil was separated by flash chromatography (1:4 ethyl acetate-hexane) to afford the crystalline product, 2-(5-bromopentyl)-1H-benzimidazole (4.16 g, 13.9 mmol, 73%), m.p. 134°–136° C. $^1H$ NMR ($CDCl_3$): 9.09 (1H, br s); 7.67 (1H, d, J=8.5 Hz); 7.34 (1H, d, J=8.8 Hz); 7.24–7.18 (2H, m); 3.40 (2H, t, J=6.6 Hz); 3.35 (2H, t, J=7.3 Hz); 1.89 (2H, t, J=7.4 Hz); 1.82 (2H, t, J=7.3 Hz); 1.68–1.58 (2H, m).

Part D. A solution of the bromide prepared in Part C above (1.88 g, 6.28 mmol), 4,5-bis(4-methoxyphenyl)-2-mercapto-1H-imidazole (1.96 g, 6.27 mmol), potassium carbonate (1.13 g, 8.18 mmol) and tetra-n-butylammonium iodide (0.46 g, 1.25 mmol) in tetrahydrofuran (50 mL) was heated to reflux for 20 hours. The mixture was cooled, and poured into water (150 mL). This was extracted with methylene chloride (2×150 mL) , and the extracts were combined, dried over anhydrous magnesium sulfate, filtered and evaporated. The residual oil was separated by flash chromatography (1:3 ethyl acetate-hexane) to afford the title product (2.49 g, 4.69 mmol, 75%), which was recrystallized to purity from ether, m.p. 85°–86° C. $^1H$ NMR ($CDCl_3$): 7.43 (2H, dd, J=6.3, 3.3 Hz); 7.39 (2H, d, J=8.8 Hz); 7.14 (2H, dd, J=6.2, 3.3 Hz); 6.79 (2H, d, J=8.8 Hz); 3.77 (6H, s); 3.20 (2H, t, J=7.3 Hz); 2.96 (2H, t, J=7.0 Hz); 1.78–1.44 (6H, m). Elemental analysis: calc. C 65.63, H 5.70, N 10.56; obs. C 65.70, H 5.60, N 10.41.

EXAMPLE 16

Preparation of 2-[5-(N-(1H-benzoxazol-2-yl)-N-heptylamino)pentyl]thio-4,5-diphenyl-1H-imidazole Method A, Part A. A solution of 2-mercapto-1H-benzoxazole (5.85 g, 38.7 mmol), methyl iodide (2.70 mL, 43.4 mmol), and potassium carbonate (7.39 g, 53.5 mmol) in tetrahydrofuran (100 mL) was heated to reflux for 18 hours. After stirring at room temperature for an additional 24 hours, the solution was poured into (2×150 mL). The extracts were combined, dried over anhydrous magnesium sulfate, filtered and evaporated to afford sufficiently pure 2-methylthio-1-H-benzoxazole (6.27 g, 37.9 mmol, 98%) as a pale yellow oil. This material was dissolved in methylene chloride (100 mL), cooled to 0° C., and treated with a solution of m-chloroperben-zoic acid (7.20 g, 41.7 mmol) in methylene chloride (40 mL). Sodium bicarbonate (about 10 g) was added, and the mixture was stirred for 18 hours. This mixture was diluted slightly with methylene chloride, then washed with aqueous sodium carbonate solution (1M, 2×150 mL) and water (150 mL). The aqueous phases were back-extracted in sequence with methylene chloride (150 mL). The organic phases were combined, dried over anhydrous magnesium sulfate, filtered, and evaporated to afford the product, 2-methylsulfonyl-1H-benzoxazole (7.04 g, 35.7 mmol, 94%), as a waxy solid. $^1$H NMR (CDCl$_3$): 8.03–7.40 (4H, m); 3.22 (3H, s).

Method A, Part B. A solution of N-[5-(4,5-diphenyl-1H-imidazol-2-ylthio)pentyl]-heptanamine (prepared according to the procedure of U.S. patent application Ser. No. 07/416,606, Billheimer et al. ) (8.57 g, 19.7 mmol), the sulfone prepared in Method A, Part A above (3.52 g, 17.9 mmol) and potassium carbonate (3.00 g, 21.7 mmol) in dimethylformamide (30 mL) was heated to 90° C. for 18 hours. The mixture was allowed to cool and poured into ethyl acetate (200 mL). This solution was washed with water (4×200 mL), and the water washings were back-extracted in sequence with ethyl acetate (200 mL). The organic phases were combined, dried over anhydrous magnesium sulfate, filtered and evaporated. The residual oil was separated by flash chromatography (1:4 ethyl acetate-hexane), and the title product was obtained as a foam from evaporation from heptane solution, m.p. 58°–60° C. (7.00 g, 12.7 mmol, 71%). $^1$H NMR (CDCl$_3$): 10.77 (1H, br s); 7.61–6.84 (14H, m); 3.52–3.40 (4H, m); 3.04 (2H, t, J=7.2 Hz); 1.79–1.58 (6H, m); 1.53–1.40 (2H, m); 1.37–1.21 (8H, m); 0.87 (3H, t, J=6.6 Hz). High-resolution mass spectrum: for C$_{34}$H$_{40}$N$_4$OS, calc. 552.2923, obs. 552.2925, diff. 0.4 ppm.

Method B. A solution of N-[5-(4,5-diphenyl-1H-imidazol-2-ylthio)pentyl]-heptanamine (2.07 g, 4.75 mmol), 2-chloro-1H-benzoxazole (0.60 mL, 5.26 mmol), and diisopropylethylamine (1.00 mL, 5.74 mmol) in 1:4 dimethylformamide-acetonitrile (30 mL) was placed in a glass-lined pressure vessel, which was pressurized to 1000 psi with nitrogen and heated to 80° C. These conditions were maintained for 24 hours, then brought to ambient conditions. The solution was poured into water (150 mL), and extracted with methylene chloride (2×150 mL). The extracts were combined, dried over anhydrous magnesium sulfate, filtered and evaporated. The residual oil was separated by flash chromatography to afford the title product (2.37 g, 4.29 mmol, 90%), which was identical to that produced by Method A above for melting point and $^1$H NMR spectrum. Elemental analysis: calc. C 73.88, H 7.29, N 10.14; obs. C 74.24, H 7.32, N 10.09.

EXAMPLE 22

Preparation of 4,5-bis(4-methoxyphenyl)-2-[5-(N-(1H-benzimidazol-2-yl)-N-heptylamino)pentyl]thio-1-H-imidazole Part A. A solution of 2-amino-1H-benzimidazole (5.00 g, 57.5 mmol) and triethylamine (7.50 mL, 53.8 mmol) in ethylene dichloride (150 mL) was treated with a solution of 5-bromovaleryl chloride (5.00 mL, 37.6 mmol) in ethylene dichloride (50 mL) with stirring, for 20 hours at ambient temperature. The solution was washed with water (2×200 mL), dried over anhydrous magnesium sulfate, filtered and evaporated to afford a solid. The solid was recrystallized from methanolacetonitrile to afford pure 5-chloro-N-(1H-benzimidazol-2-yl)-pentanamide, m.p. 161°–163° C. (2.98 g, 11.8 mmol). $^1$H NMR (d$^6$-DMSO): 12.14 (1H, br s); 11.56 (1H, br s); 7.44 (2H, dd, J=5.9, 3.0 Hz); 7.08 (2H, dd, J=5.8, 2.9 Hz); 3.58 (2H, t, J=6.6 Hz); 2.49 (2H, t, J=6.9 Hz); 1.96–1.71 (4H, m). Successive crops of solid from the mother liquor proved to be 5-bromo-N-(1H-benzimidazol-2-yl)-pentanamide (2.85 g, 9.62 mmol; total yield of products 58%).

Part B. A solution of the halide prepared in Part A above (as a mixture of chloride and bromide, 4.59 mmol), 4,5-bis(4-methoxyphenyl)-2-mercapto-1H-imidazole (1.43 g, 4.58 mmol), potassium carbonate (0.82 g, 5.93 mmol) and sodium iodide (0.21 g, 1.40 mmol) in dimethylformamide (15 mL) was heated to 80° C. for 24 hours. The solution was cooled, and poured into ethyl acetate (200 mL). This was washed with water (3×200 mL). The aqueous phases were back-extracted in sequence with methylene chloride (200 mL). The organic phases were combined, dried over anhydrous magnesium sulfate, filtered and evaporated. The residual oil was separated by flash chromatography (1:1 ethyl acetate-hexane )to afford the product, N-(1H-benzimidazol-2-yl)-5-[4,5-bis(4-methoxyphenyl)-1H-imidazol-2-ylthio]pentanamide, as a gum (0.9 g, 1.76 mmol, 38%). $^1$H NMR (CDCl$_3$): 7.53–7.32 (6H, m); 7.16 (2H, dd, J=5.9, 3.3 Hz); 6.88–6.78 (4H, m); 3.78 (6H, s); 3.10 (2H, t, J=6.6 Hz); 2.59 (2H, t, J=6.6 Hz); 2.01–1.91 (2H, m); 1.88–1.78 (2H, m).

Part C. A solution of the amide prepared in Part B above (0.93 g, 1.76 mmol) in tetrahydrofuran (20 mL) was added to a solution of sodium bis(methoxyethoxy)aluminum hydride (1.50 mL of a commercial 3.4M solution in toluene, 5.10 mmol) in tetrahydrofuran (20 mL) at 0° C. The mixture was then warmed to mild reflux for 2 hours, then cooled to ambient temperature and stirred for an additional 20 hours. The excess reagent was carefully quenched by the addition of aqueous sodium hydroxide solution (5 mL of 2N). The mixture was partitioned between methylene chloride and water (100 mL each), and the aqueous phase was extracted with methylene chloride (100 mL). The organic phases were combined, dried over anhydrous potassium carbonate, filtered and evaporated.

The residue thus obtained was dissolved in 1:1 dimethylformamide-tetrahydrofuran (20 mL), and treated with heptyl iodide (0.35 mL, 2.14 mmol) and diisopropylethylamine (0.50 mL, 2.87 mmol). The solution was heated to 85° C. for 20 hours, then cooled and poured into ethyl acetate (100 mL). This solution was washed with water (3×150 mL), dried over anhydrous potassium carbonate, filtered and evaporated. The residue was separated by flash chromatography to afford the title product as a solid, m.p. 78°–80° C. (0.48 g, 0.78 mmol, 44%). ¹H NMR (CDCl₃): 7.40 (4H, d, J=8.4 Hz); 7.33 (2H, d, J=6.9 Hz); 7.09–6.97 (3H, br m); 6.78 (4H, d, J=8.4 Hz); 4.87 (1H, br s); 3.80 (2H, t, J=6.5 Hz); 3.77 (6H, s); 3.56 (2H, q, J=5.9 Hz); 2.97 (2H, t, J=7.2 Hz); 1.78–1.55 (8H, m); 1.32–1.17 (8H, m); 0.85 (3H, t, J=7.0 Hz).

Compounds 1–90 in Table 1 (below) can be prepared by the procedures described in Examples 2, 16 and 22 employing the appropriately substituted starting materials.

EXAMPLE 152

Preparation of 4,5-bis(4-methoxyphenyl)-2-[(3-(1H-benzoxazol-2-ylthio)methyl)benzyl]thio-1H-imidazole Part A. A solution of ethyl 3-methylbenzoate (17.0 mL, 107 mmol), N-bromosuccinimide (19.0 g, 107 mmol), and azoisobutyonitrile (0.5 g) in carbon tetrachloride (200 mL) was heated to reflux for 20 hours, then cooled. The mixture was evaporated, and the residue was eluted though a short plug of silica gel with 1:9 ethyl acetate-hexane to afford an oily mixture of compounds. Analysis by ¹H NMR spectroscopy showed a 70.2:16.5:13.3 molar mixture of ethyl 3-(bromomethyl)benzoate, ethyl 3-(dibromomethyl)benzoate, and ethyl 3-methylbenzoate, respectively. (Yield of the product therefore 19.0 g, 78.0 mmol, 73%).

A solution of the material prepared above, 4,5-bis(4-methoxyphenyl)-2-mercapto-1H-imidazole (24.4 g, 78.0 mmol), potassium carbonate (14.0 g, 101 mmol) and tetra-n-butylammonium iodide (5.76 g, 15.6 mmol) in tetrahydrofuran (150 mL) was heated to reflux for 20 hours, then cooled and poured into an equal volume of water. This was extracted with methylene chloride (150 mL), and the aqueous phase was neutralized to pH 7 with aqueous HCl (6N), saturated with sodium chloride and re-extracted with methylene chloride (150 mL). The extracts were combined, dried over anhydrous magnesium sulfate, filtered and evaporated. The resulting solid was recrystallized to purity from acetonitrile in two crops (25.0 g, 52.8 mmol, 68%), to give ethyl 3-[(4,5-bis(4-methoxyphenyl)-1H-imidazol-2-ylthio)methyl]benzoate, m.p. 147°–149° C. ¹H NMR (CDCl₃): 9.02 (1H, br s); 8.00–7.90 (2H, m); 7.61–7.02 (5H, m); 6.83 (4H, d, J=8.0 Hz); 4.32 (2H, q, J=7.4 Hz); 4.25 (2H, s); 3.81 (6H, s); 1.34 (3H, t, J=7.4 Hz).

Part B. A solution of the ester prepared in Part A above (6.57 g, 13.8 mmol) in tetrahydrofuran (20 mL) was added to an ice-cooled slurry of lithium aluminum hydride (1.16 g, 30.5 mmol) in tetrahydrofuran (20 mL). The mixture was warmed to mild reflux for 18 hours, then re-cooled to 0° C. and quenched by the careful sequential addition of water (2 mL), 15% aqueous sodium hydroxide (6 mL), and water (6 mL). The resulting mixture was filtered through celite, dried over anhydrous potassium carbonate, filtered and evaporated to afford the product, 4,5-bis(4-methoxyphenyl)-2-[3-(hydroxymethyl)benzyl]thio-1-H-imidazole, as an oil (5.97 g, 13.8 mmol, 100%). ¹H NMR (CDCl₃): 7.41–7.07 (8H, m); 6.81 (4H, d, J=8.8 Hz); 4.56 (2H, s); 4.15 (2H, s); 3.79 (6H, s).

Part C. A solution of the alcohol prepared above (5.96 g, 13.8 mmol), diisopropylethylamine (2.90 mL, 16.6 mmol) and toluenesulfonyl chloride (2.89 g, 15.2 mmol) in tetrahydrofuran (30 mL) was heated to reflux for 18 hours. The mixture was cooled, and poured into water (150 mL). This was extracted with methylene chloride (2×150 mL), and the extracts were combined, dried over magnesium sulfate and evaporated. The residual oil was separated by flash chromatography (3:7 ethyl acetate-hexane)to afford the product, 4,5-bis (4-methoxyphenyl)-2-[3-(chloro-methyl)benzyl]thio-1H-imidazole, as a foam upon vacuum pumping (2.24 g, 4.96 mmol, 36%). ¹H NMR (CDCl₃): 8.94 (1H, br s); 7.70–7.09 (8H, m); 6.84 (4H, d, J=8.8 Hz); 4.51 (2H, s); 4.19 (2H, s); 3.81 (6H, s).

Part D. A solution of the chloride prepared above (1.10 g, 2.44 mmol), 2-mercapto-1H-benzoxazole (0.37 g, 2.44 mmol), potassium carbonate (0.42 g, 2.93 mmol) and tetra-n-butylammonium iodide (0.94 g, 2.44 mmol) in tetrahydrofuran (20 mL) was heated to reflux for 20 hours, then cooled. It was poured into water (150 mL), and extracted with methylene chloride (150 mL). The aqueous phase was neutralized to pH 7, and re-extracted. The extracts were combined, dried over anhydrous magnesium sulfate, filtered and evaporated. The residual oil was separated by flash chromatography (3:7 ethyl acetate-hexane)to afford the title product as a crystalline solid, m.p. 129°–131° C. ¹H NMR (CDCl₃): 9.04 (1H, br s); 7.54–6.70 (16H, m); 4.46 (2H, s); 4.15 (2H, s); 3.79 (3H, s); 3.78 (3H, s). Elemental analysis: calc. C 67.94, H 4.81, N 7.43; obs. C 67.64, H 4.71, N 7.34.

Compounds 91–180 in Table 2 (below) can be prepared by the procedure described in Example 152 employing the appropriately substituted starting materials.

EXAMPLE 183

Preparation of 4,5-bis(4-dimethylaminophenyl)-2-[5-(2-(1-methylethyl)-1H-benzimidazol-1-yl)pentyl]thio-1-H-imidazole Part A. Sodium hydride (1.62 g of a 50% slurry, 33.8 mmol) was washed with hexane and dried under vacuum. Dimethylformamide (50 mL) was added, followed by a solution of 2-isopropyl-1H-benzimidazole (5.41 g, 33.8 mmol) in dimethylformamide (15 mL). After stirring at ambient temperature for two hours, the mixture was treated with ethyl 5-bromovalerate (5.50 mL, 34.8 mmol) and sodium iodide (1.19 g, 7.94 mmol). The mixture was heated to 80° C. for 18 hours, then cooled and poured into ethyl acetate (200 mL). This was washed with water (4×200 mL), then brine (200 mL), and dried over anhydrous magnesium sulfate, filtered and evaporated. The product, 1-(4-carboethoxybutyl)-2-(1-methylethyl)-1H-benzimidazole, was obtained as an oil after purification by silica gel chromatography (1:2 ethyl acetate-hexane) (9.54 g, 33.1 mmol, 98%). ¹H NMR (CDCl₃): 7.75 (1H, dd, J=5.6, 3.1 Hz); 7.34–7.19 (3H, m); 4.12 (2H, q, J=7.1 Hz); 1.92–1.80 (2H, m); 1.78–1.65 (2H, m); 1.45 (6H, d, J=6.6 Hz); 1.24 (3H, t, J=7.0 Hz).

Part B. A solution of the ester obtained in Part A above (9.54 g, 33.1 mmol) in tetrahydrofuran (30 mL) was added to a solution of lithium aluminum hydride (80 mmol) in tetrahydrofuran (80 mL) at 0° C. The mixture was heated to reflux overnight, then cooled back to 0° C. and quenched by the careful sequential addition of water (3 mL), then aqueous sodium hydroxide solution (10 mL of 15%), then water (10 mL). The mixture was filtered through celite with copius tetrahydrofuran washing, and the liquid was dried over anhydrous potassium carbonate, filtered and evaporated. The residual oil was separated by flash chromatography (ethyl acetate) to afford the product, 1-(5-hydroxypentyl)-2-(1-methylethyl)-1H-benzimidazole (6.82 g, 27.7 mmol, 84%) as an oil. $^1$H NMR (CDCl$_3$) : 7.78–7.70 (1H, m); 7.32–7.22 (3H, m); 4.90 (1H, br d, J=2.2 Hz); 4.12 (2H, t, J=7.5 Hz); 3.64 (2H, t, J=6.0 Hz); 3.18 (1H, m, J=6.6 Hz); 1.93–1.45 (6H, m); 1.44 (6H, d, J=6.6 Hz).

Part C. A solution of the alcohol prepared in Part B above (4.18 g, 17.0 mmol) and carbon tetrabromide (6.75 g, 20.3 mmol) in methylene chloride (40 mL) was cooled to 0° C., and a solution of triphenylphosphine (5.34 g, 20.4 mmol) in methylene chloride (40 mL) was added dropwise. The mixture was stirred for 20 hours, then evaporated. The residue was separated by flash chromatography (1:2 ethyl acetate-hexane) to afford the product, 1-(5-bromopentyl)-2-(1-methylethyl)-1H-benzimidazole, as an oil (4.80 g, 15.5 mmol, 92%). $^1$H NMR (CDCl$_3$): 7.79–7.72 (1H, m) ; 7.32–7.21 (3H, m); 4.14 (2H, t, J=7.5 Hz); 3.39 (2H, t, J=6.6 Hz); 3.18 (1H, heptet, J=7.0 Hz); 1.94–1.78 (4H, m); 1.63–1.50 (2H, m); 1.45 (6H, d, J=7.0 Hz).

Part D. A solution of the bromide prepared in Part C above (2.40 g, 7.76 mmol), 4,5-bis(4-dimethylaminophenyl)-2-mercapto-1H-imidazole (2.39 g, 7.06 mmol), potassium carbonate (1.29 g, 9.33 mmol), and tetra-n-butylammonium iodide (0.44 g) in tetrahydrofuran (20 mL) was heated to reflux for 18 hours. The mixture was cooled, and partitioned between water and methylene chloride (100 mL each). The organic phase was dried over anhydrous potassium carbonate, filtered and evaporated. The title product was obtained, after flash chromatography (1:1 ethyl acetate-hexane) and evaporation from ether solution, as a solid foam, m.p. 110°–112° C. (2.42 g, 4.27 mmol, 55%). $^1$H NMR (CDCl$_3$): 8.83 (1H, br s); 7.73 (1H, dd, J=6.2, 2.9 Hz); 7.60–7.20 (7H, m); 6.64 (4H, br); 4.12 (2H, t, J=7.0 Hz); 3.17 (1H, heptet, J=7.0 Hz); 2.96 (12H, br s); 1.95–1.77 (2H, m); 1.65–1.52 (4H, m); 1.43 (6H, d, J=7.0 Hz).

Compounds 181–280 in Table 3 can be prepared by the procedure described in Example 183 employing the approximately substituted starting materials.

EXAMPLE 287

Preparation of 4,5-bis(4-methoxyphenyl)-2-[4-(2-methyl-1H-benzimidazol-1-yl)methyl]benzylthio-1-H-imidazole Part A. Sodium hydride is washed with hexane and dried under vacuum. DMSO (1 mL/mmol sodium hydride) is added, and the mixture is cooled to 0° C. A solution of 2-methyl-1H-benzimidazole (1 eq.) in DMSO (1 mL/mmol) is added dropwise, and the mixture is warmed to room temperature and stirred until nitrogen gas evolution is complete. Then, the mixture is treated with 3-methyl benzyl bromide (1 eq.). This solution is stirred overnight at 80° C., then cooled to ambient temperature and poured into ethyl acetate (4 mL/mL reaction mixture). This is washed with equal volumes of water (4×), dried over anhydrous magnesium sulfate, filtered and evaporated. The product, 1-(3-methylbenzyl)-2-methyl-1H-benzimidazole, may be purified by column chromatography, using an appropriate solvent as determined by thin-layer chromatography.

Part B. A solution of the compound prepared in Part A above, N-bromosuccinimide (1 eq.) and azoisobutyonitrile (0.1 eq.) in carbon tetrachloride (2 mL/mmol substrate) is heated to reflux for at least 18 hours. The solution is then cooled, filtered and evaporated, and the residue eluted through a plug of silica gel with an appropriate solvent. Evaporation then affords 1-(3-bromomethylbenzyl)-2-methyl-1H-benzimidazole.

Part C. The bromide compound prepared in Part B above is dissolved along with 4,5-bis(4-methoxyphenyl)-2-mercapto-1H-imidazole (1 eq. ) and potassium carbonate (1.3 eq.) in tetrahydrofuran (2 mL/mmol substrate). The solution is heated to mild reflux overnight. The reaction mixture is cooled, and poured into 4 volumes of water. This is extracted with 2 equal volumes of methylene chloride, and the extracts are combined, dried over anhydrous magnesium sulfate, filtered and evaporated. The title product may then be isolated by column chromatography, and purified by recrystallization from an appropriate solvent.

Compounds 281–364 in Table 4 can be prepared by the procedure described in Example 287 employing the appropriately substituted starting materials.

EXAMPLE 381

Preparation of 6-[N-(5-(4,5-diphenyl-1H-imidazol-2-ylthio)pentyl)-N-heptylamino]-purine A solution of N-[5-(4,5-diphenyl-1H-imidazol-2-ylthio)pentyl]-heptanamine (5.30 g, 12.2 mmol), 6-chloropurine (1.90 g, 12.3 mmol), and diisopropylamine (3.00 mL, 17.2 mmol) in acetonitrile (50 mL) was heated to mild reflux for 18 hours, and then cooled and poured into water (200 mL). This was extracted with methylene chloride (2×200 mL), and the extracts were combined, dried over anhydrous potassium carbonate, filtered and evaporated. The residue was separated by flash chromatography (ethyl acetate) to afford the title product as a solid, m.p. 58°–60° C. $^1$H NMR (CDCl$_3$): 10.66 (2H, br s); 8.30 (1H, s); 7.83 (1H, s); 7.67–7.18 (10H, m); 4.10 (4H, br); 3.08 (2H, t, J=7.1 Hz); 1.80–1.20 (16 H, m); 0.89 (3H, t, J=6.6 Hz). High-resolution mass spectrum: calc. for C$_{32}$H$_{39}$N$_7$S 554.3066, obs. 554.3053, diff. 2.3 ppm.

Compounds 381–458 in Table 5 can be prepared by the procedure described in Example 381 employing the appropriately substituted starting materials.

EXAMPLE 477

Preparation of 6-[3-[[4,5-bis(4-methoxyphenyl)-1H-imidazol-2-ylthio]-methyl]benzylthio]-purine A solution of 4,5-bis(4-methoxyphenyl)-2-mercapto-1H-imidazole (3.00 g, 9.60 mmol), 6-mercaptopurine (1.63 g, 9.60 mmol) a,a'-dibromoxylene (2.54 g, 9.60 mmol), and potassium carbonate (3.32 g, 24.0 mmol) and in 5:1 tetrahydrofuran-dimethylformamide (12 mL) was heated to reflux for 20 hours, then cooled. It was poured into ethyl acetate (150 mL), and washed with water (4×150 mL). The aqueous phases were back-extracted in sequence with ethyl acetate. The extracts were combined, dried over anhydrous magnesium sulfate, filtered and evaporated. The residual oil was separated by flash chromatography (ethyl acetate) to afford the title product as a crystalline solid, m.p. 129°–130° C. (1.64 g, 2.89 mmol, 30%). $^1$H NMR (CDCl$_3$): 8.63 (1H, s); 8.02 (1H, s); 7.30 (4H, d, J=8.8 Hz); 7.23 (1H, s); 7.16 (1H, d, J=8 Hz); 6.99 (1H, t, J=8 Hz); 6.81 (1H, d, J=8 Hz); 6.71 (4H, d, J=8.8 Hz); 4.44 (2H, s); 4.02 (2H, s); 3.69 (6H, s). Elemental analysis: calculated C 63.58, H 4.62, N 14.83; observed C 63.25, H 4.55, N 14.72.

Compounds 461–540 in Table 6 can be prepared by the procedure described in Example 477 employing the appropriately substituted starting materials.

Utility

The compounds of the invention are effective antiatherosclerotic agents that act in a variety of ways. The compounds may be inhibitors of the enzyme acyl CoA:-cholesterol acyl transferase (ACAT). Inhibition of ACAT has a variety of antiatherosclerotic effects, including inhibiting esterification and transport of cholesterol across the intestinal wall. In addition, by inhibiting cholesterol ester formation, the compounds may be useful in preventing the formation of cholesterol ester rich macrophages (foam cells) in the arterial wall. Foam cells are a source of the large quantity of cholesterol ester found in atheromatous lesions, as compared to the surrounding undiseased tissue. Other compounds of the invention may be inhibitors of cholesterol biosynthesis in the liver. Some compounds of the invention are both ACTA inhibitors and inhibitors of cholesterol biosynthesis.

A. Assay of the Inhibition of Acyl-CoA: Cholesterol Acyltransferase (ACAT) in Hepatic Microsomes The ability of the compounds to inhibit ACAT, the enzyme responsible for the intracellular synthesis of cholesteryl esters, was tested as follows. Male Sprague Dawley rats weighing 150–300 g, were fed rat chow ad libitum. The animals were fasted for twenty-four hours prior to being sacrificed by decapitation. The livers were perfused in situ with 50 ml of cold 0.25 sucrose, excised, and homogenized in three volumes of 0.1M phosphate buffer, pH 7.4, that contained 0.5 mM EDTA (ethylenediamine-tetraacetic acid), 1.0 mM glutathione, 0.25M sucrose and 20 mM leupeptin. Microsomes were obtained by differential centrifugation; the supernatant from an initial spin at 15,000×g for 15 minutes was centrifuged at 105,000×g for 1 hour to pellet the microsomes. The microsomes were suspended in homogenization buffer, reisolated by centrifugation, and stored at $-70°$ C. Microsomes were used within one month of preparation.

The control assay in a final volume of 200 μl consisted of 200 μg of microsomal protein, 75 μM $^{14}$C-oleoyl-CoA (10,000 dpm/nmol) in 0.1M phosphate, pH 7.4, that contained 1 mM glutathione. Compounds were added in 5 μl of DMSO (dimethyl sulfoxide) and additional controls were run with DMSO only. All components, except the oleoyl-CoA, were preincubated for 15 min. at 37° C. prior to the initiation of the reaction by the addition of oleoyl-CoA. The assay was terminated after 10 min by the addition of 4 ml of chloroform:methanol (2:1, v/v). 20,000 dpm of $^{3}$H-cholesteryl oleate and 10 μg of unlabeled cholesteryl oleate and oleic acid were added as an internal standard and carriers, respectively. After allowing 10 min. for lipid extraction, the samples were centrifuged at 1,000×g for 10 min to separate the solvent layers. The chloroform layer containing the neutral lipids was spotted onto a Baker SI250-Pa silica gel TLC plate and the plate developed using a hexane:diethyl ether:acetic acid (170:30:1) v/v/v) mobile phase. The lipids were visualized by their interaction with iodine vapor and the cholesteryl ester spot was scraped into a scintillation vial and counted. The specific activity of ACAT in the control incubation averaged 260 pmol/min/mg microsomal protein. The data obtained are expressed as the concentration at which ACAT activity is inhibited by 50% ($IC_{50}$).

B. Assay of the Inhibition of Cholesterol Esterification in Mammalian Cells

The esterification of cholesterol was determined in the murine macrophage-like cell line J774.A1. Cells were seeded in 35 mm wells at a density of 300,000 cells per well in 2 mls of Dulbecco's Eagle Medium (DMEM) supplemented with 10% fetal bovine serum (FBS). Cells were incubated at 37° C. in an atmosphere of 5% $CO_2$ and 93% humidity. After 24 hours the media was changed to 0.68 mls 10% FBS-DMEM containing 34 μg of acetylated human low density lipoprotein (ac-LDL) to increase the intracellular concentration of cholesterol and promote esterification. At 41 hours, various inhibitors were added to the cells in DMSO (10 μl/ml maximum). At 43 hours, the cells were pulsed with 0.1 mM $^{14}$C-oleic acid (10,000 dpm/nmol) complexed with BSA (bovine serum albumin) to follow cholesterol ester formation. The experiment was terminated at 45 hours by washing the monolayers 3 times with 3 ml of Tris-buffered saline at 4° C. The lipids were extracted by incubating the monolayers with 1.5 ml of hexane:isopropanol (3:2, v/v) for 30 min. under gentle agitation. During this period, 10,000 dpm 3H-cholesteryl linoleate and 10 μg of cholesteryl oleate were added as an internal standard and carrier respectively. The organic solvent was removed and the cells were washed with an additional 1.0 ml of hexane:isopropanol which was combined with the original extract. The cells were allowed to dry overnight, digested with 1.5 ml of 0.2N sodium hydroxide for 1 hour and an aliquot of the solubilized protein used for protein determination using the Lowry method. The organic extract was taken to dryness, the residue resuspended in 100 μl of chloroform and the lipids separated on silica gel impregnated glass fiber plates using a hexane:diethylether:acetic acid (170:30:1, v/v/v) solvent system. Individual lipids were visualized with iodine and the cholesteryl ester spot cut out and transferred to scintillation vials to determine the amount of radioactivity. The conversion of oleic acid to cholesteryl ester in the control averaged 0.54 mmol/-hour/mg protein and was increased upon the addition of ac-LDL to about 10.69±0.69 mmol/hour/mg protein. The data obtained are expressed as the concentration at which ACAT activity is inhibited by 50% ($IC_{50}$).

C. Assay of Antihypercholesterolemic Activity in Cholesterol-Fed Hamsters

Inhibiton of ACAT activity in the gut reduces the absorption of cholesterol in cholesterol-fed animals. Hamsters weighing approximately 100 g, were maintained on a diet supplemented with 0.8% cholesterol. The treatment group received 1–100 mg/kg/day, p.o., of the test compound dissolved in 500 μl of corn oil for a period of two weeks. The control group were pair-fed to the treatment group and were dosed with 500 μl of the corn oil vehicle. At sacrifice, the hamsters were anesthetized with $CO_2$ and exsanguinated via cardiac puncture. Total serum cholesterol was determined on a DuPont aca TM IV. The data obtained are expressed in terms of mg cholesterol per 100 ml of serum (mg %).

Using the assay methods described above, the compounds of this invention are found to exhibit an activity of at least IC50<50 micromolar, thereby demonstrating and confirming the activity of these compound as effective antihypercholesterolemic and/or antiatherosclerotic agents.

Dosage Forms

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is *Remington's Pharmaceutical Sciences,* Mack Publishing.

In their therapeutic use as antihypercholesterolemic and/or anti- atherosclerotic agents, the compounds of the invention are administered to the patient at dosage levels of 1 to 28 g per day. For a normal male adult human of approximately 70 kg of body weight, this translates into a dosage of 14 to 400 mg per kilogram body weight per day. The dosage administered will, of course, vary depending upon known factors such as the age, health, and weight of the recipient; nature and extent of symptoms, kind of concurrent treatment, frequency of treatment, and the effect desired. Useful pharmaceutical dosage forms for administration of the compounds of this invention can be illustrated as follows:

Tablets: Tablets may be prepared by conventional procedures so that the dosage unit is 500 milligrams of active ingredient, 150 milligrams of lactose, 50 milligrams of cellulose and 10 milligrams of magnesium stearate.

Capsules: Capsules are prepared by conventional procedures so that the dosage unit is 500 milligrams of active ingredient, 100 milligrams of cellulose and 10 milligrams of magnesium stearate.

Syrup:

|  | Wt. % |
| --- | --- |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

Aqueous Suspension:

|  | Wt. % |
| --- | --- |
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

Resuspendable Powder:

|  | Wt. % |
| --- | --- |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

Sem-Solid Gel

|  | Wt. % |
| --- | --- |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

Sem-Solid Paste:

|  | Wt. % |
| --- | --- |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin ® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

Emulsifiable Paste:

|  | Wt. % |
| --- | --- |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

The term "consisting essentially of" in the present disclosure is intended to have its customary meaning; namely, that all specified materials and conditions are very important in practicing the invention but that unspecified materials and conditions are not excluded so long as they do not prevent the benefits of the invention from being realized.

The foregoing disclosure includes all the information deemed essential to enable those of skill in the art to practice the claimed invention. Because the cited references may provide further useful information, however, these cited materials are hereby incorporated by reference.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

TABLE 1

$$\begin{array}{c} R^1 \\ \diagdown \\ R^2 \end{array} \begin{array}{c} N \\ \diagup \\ N \\ | \\ R^3 \end{array} - X-(CH_2)_{m+n+1}-Y- \begin{array}{c} N \\ \diagup \\ A \end{array} \begin{array}{c} D \\ \diagdown \\ B \end{array}$$

| Ex. | R¹ | R² | R³ | X | m + n + 1 | Y | A | B | D | m.p. |
|---|---|---|---|---|---|---|---|---|---|---|
| 1 | Ph | Ph | H | S | 5 | S | NH | CH | CH | — |
| 2 | 4-MeO—C₆H₄ | 4-MeO—C₆H₄ | H | S | 5 | S | NH | CH | CH | 85–86 |
| 3 | 4-Me₂N—C₆H₄ | 4-Me₂N—C₆H₄ | H | S | 5 | S | NH | CH | CH | — |
| 4 | 4-MeS—C₆H₄ | 4-MeS—C₆H₄ | H | S | 5 | S | NH | CH | CH | — |
| 5 | iPr | iPr | H | S | 5 | S | NH | CH | CH | — |
| 6 | Ph | Ph | H | S | 5 | S | NH | N | CH | — |
| 7 | 4-MeO—C₆H₄ | 4-MeO—C₆H₄ | H | S | 5 | S | NH | N | CH | — |
| 8 | 4-Me₂N—C₆H₄ | 4-Me₂N—C₆H₄ | H | S | 5 | S | NH | N | CH | — |
| 9 | 4-MeS—C₆H₄ | 4-MeS—C₆H₄ | H | S | 5 | S | NH | N | CH | — |
| 10 | iPr | iPr | H | S | 5 | S | NH | N | CH | — |
| 11 | Ph | Ph | H | S | 5 | S | NH | N | N | — |
| 12 | 4-MeO—C₆H₄ | 4-MeO—C₆H₄ | H | S | 5 | S | NH | N | N | — |
| 13 | 4-Me₂N—C₆H₄ | 4-Me₂N—C₆H₄ | H | S | 5 | S | NH | N | N | — |
| 14 | 4-MeS—C₆H₄ | 4-MeS—C₆H₄ | H | S | 5 | S | NH | N | N | — |
| 15 | iPr | iPr | H | S | 5 | S | NH | N | N | — |
| 16 | Ph | Ph | H | S | 5 | N—C₇H₁₅ | O | CH | CH | 58–60 |
| 17 | 4-MeO—C₆H₄ | 4-MeO—C₆H₄ | H | S | 5 | N—C₇H₁₅ | O | CH | CH | oil$^a$ |
| 18 | 4-Me₂N—C₆H₄ | 4-Me₂N—C₆H₄ | H | S | 5 | N—C₇H₁₅ | O | CH | CH | — |
| 19 | 4-MeS—C₆H₄ | 4-MeS—C₆H₄ | H | S | 5 | N—C₇H₁₅ | O | CH | CH | — |
| 20 | iPr | iPr | H | S | 5 | N—C₇H₁₅ | O | CH | CH | — |
| 21 | Ph | Ph | H | S | 5 | N—C₇H₁₅ | NH | CH | CH | — |
| 22 | 4-MeO—C₆H₄ | 4-MeO—C₆H₄ | H | S | 5 | N—C₇H₁₅ | NH | CH | CH | 78–80 |
| 23 | 4-Me₂N—C₆H₄ | 4-Me₂N—C₆H₄ | H | S | 5 | N—C₇H₁₅ | NH | CH | CH | — |
| 24 | 4-MeS—C₆H₄ | 4-MeS—C₆H₄ | H | S | 5 | N—C₇H₁₅ | NH | CH | CH | — |
| 25 | iPr | iPr | H | S | 5 | N—C₇H₁₅ | NH | CH | CH | — |
| 26 | Ph | Ph | H | S | 5 | N—C₇H₁₅ | S | CH | CH | 65–67 |
| 27 | 4-MeO—C₆H₄ | 4-MeO—C₆H₄ | H | S | 5 | N—C₇H₁₅ | S | CH | CH | — |
| 28 | 4-Me₂N—C₆H₄ | 4-Me₂N—C₆H₄ | H | S | 5 | N—C₇H₁₅ | S | CH | CH | — |
| 29 | 4-MeS—C₆H₄ | 4-MeS—C₆H₄ | H | S | 5 | N—C₇H₁₅ | S | CH | CH | — |
| 30 | iPr | iPr | H | S | 5 | N—C₇H₁₅ | S | CH | CH | — |
| 31 | Ph | Ph | H | S | 5 | N(CH₂)₂O—(CH₂)₂OMe | O | CH | CH | — |
| 32 | 4-MeO—C₆H₄ | 4-MeO—C₆H₄ | H | S | 5 | N(CH₂)₂O—(CH₂)₂OMe | O | CH | CH | oil$^b$ |
| 33 | 4-Me₂N—C₆H₄ | 4-Me₂N—C₆H₄ | H | S | 5 | N(CH₂)₂O—(CH₂)₂OMe | O | CH | CH | — |
| 34 | 4-MeS—C₆H₄ | 4-MeS—C₆H₄ | H | S | 5 | N(CH₂)₂O—(CH₂)₂OMe | O | CH | CH | — |
| 35 | iPr | iPr | H | S | 5 | N(CH₂)₂O—(CH₂)₂OMe | O | CH | CH | — |
| 36 | Ph | Ph | H | S | 5 | N(CH₂)₂O—(CH₂)₂OMe | NH | CH | CH | — |
| 37 | 4-MeO—C₆H₄ | 4-MeO—C₆H₄ | H | S | 5 | N(CH₂)₂O—(CH₂)₂OMe | NH | CH | CH | — |
| 38 | 4-Me₂N—C₆H₄ | 4-Me₂N—C₆H₄ | H | S | 5 | N(CH₂)₂O—(CH₂)₂OMe | NH | CH | CH | — |
| 39 | 4-MeS—C₆H₄ | 4-MeS—C₆H₄ | H | S | 5 | N(CH₂)₂O—(CH₂)₂OMe | NH | CH | CH | — |
| 40 | iPr | iPr | H | S | 5 | N(CH₂)₂O—(CH₂)₂OMe | NH | CH | CH | — |
| 41 | Ph | Ph | H | S | 5 | N(CH₂)₂O—(CH₂)₂OMe | S | CH | CH | — |
| 42 | 4-MeO—C₆H₄ | 4-MeO—C₆H₄ | H | S | 5 | N(CH₂)₂O—(CH₂)₂OMe | S | CH | CH | — |
| 43 | 4-Me₂N—C₆H₄ | 4-Me₂N—C₆H₄ | H | S | 5 | N(CH₂)₂O—(CH₂)₂OMe | S | CH | CH | — |
| 44 | 4-MeS—C₆H₄ | 4-MeS—C₆H₄ | H | S | 5 | N(CH₂)₂O—(CH₂)₂OMe | S | CH | CH | — |
| 45 | iPr | iPr | H | S | 5 | N(CH₂)₂O—(CH₂)₂OMe | S | CH | CH | — |
| 46 | Ph | Ph | H | S | 5 | N—C₇H₁₅ | NH | N | N | — |
| 47 | 4-MeO—C₆H₄ | 4-MeO—C₆H₄ | H | S | 5 | N—C₇H₁₅ | NH | N | N | — |
| 48 | 4-Me₂N—C₆H₄ | 4-Me₂N—C₆H₄ | H | S | 5 | N—C₇H₁₅ | NH | N | N | — |
| 49 | 4-MeS—C₆H₄ | 4-MeS—C₆H₄ | H | S | 5 | N—C₇H₁₅ | NH | N | N | — |
| 50 | iPr | iPr | H | S | 5 | N—C₇H₁₅ | NH | N | N | — |
| 51 | Ph | Ph | H | S | 5 | CH₂ | O | CH | CH | — |
| 52 | 4-MeO—C₆H₄ | 4-MeO—C₆H₄ | H | S | 5 | CH₂ | O | CH | CH | — |
| 53 | 4-Me₂N—C₆H₄ | 4-Me₂N—C₆H₄ | H | S | 5 | CH₂ | O | CH | CH | — |
| 54 | 4-MeS—C₆H₄ | 4-MeS—C₆H₄ | H | S | 5 | CH₂ | O | CH | CH | — |
| 55 | iPr | iPr | H | S | 5 | CH₂ | O | CH | CH | — |
| 56 | Ph | Ph | H | SO₂ | 5 | SO₂ | NH | CH | CH | — |
| 57 | 4-MeO—C₆H₄ | 4-MeO—C₆H₄ | H | SO₂ | 5 | SO₂ | NH | CH | CH | — |
| 58 | 4-Me₂N—C₆H₄ | 4-Me₂N—C₆H₄ | H | SO₂ | 5 | SO₂ | NH | CH | CH | — |
| 59 | 4-MeS—C₆H₄ | 4-MeS—C₆H₄ | H | SO₂ | 5 | SO₂ | NH | CH | CH | — |
| 60 | iPr | iPr | H | SO₂ | 5 | SO₂ | NH | CH | CH | — |
| 61 | Ph | Ph | H | S | 3 | S | NH | CH | CH | — |
| 62 | 4-MeO—C₆H₄ | 4-MeO—C₆H₄ | H | S | 3 | S | NH | CH | CH | — |
| 63 | 4-Me₂N—C₆H₄ | 4-Me₂N—C₆H₄ | H | S | 3 | S | NH | CH | CH | — |
| 64 | Ph | Ph | H | S | 8 | S | NH | CH | CH | — |
| 65 | 4-MeO—C₆H₄ | 4-MeO—C₆H₄ | H | S | 8 | S | NH | CH | CH | — |
| 66 | 4-Me₂N—C₆H₄ | 4-Me₂N—C₆H₄ | H | S | 8 | S | NH | CH | CH | — |
| 67 | Ph | Ph | CH₃ | S | 5 | S | NH | CH | CH | — |
| 68 | 4-MeO—C₆H₄ | 4-MeO—C₆H₄ | CH₃ | S | 5 | S | NH | CH | CH | — |
| 69 | 4-Me₂N—C₆H₄ | 4-Me₂N—C₆H₄ | CH₃ | S | 5 | S | NH | CH | CH | — |
| 70 | 4-MeS—C₆H₄ | iPr | H | S | 5 | S | NH | CH | CH | — |

TABLE 1-continued

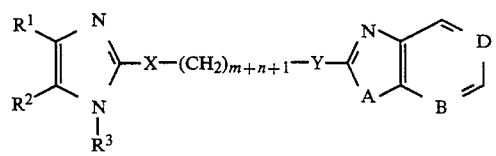

| Ex. | R¹ | R² | R³ | X | m + n + 1 | Y | A | B | D | m.p. |
|---|---|---|---|---|---|---|---|---|---|---|
| 71 | Ph | Ph | H | S | 5 | N(CH₂)₂O—(CH₂)₃CH₃ | O | CH | CH | — |
| 72 | 4-MeO—C₆H₄ | 4-MeO—C₆H₄ | H | S | 5 | N(CH₂)₂O—(CH₂)₃CH₃ | O | CH | CH | — |
| 73 | 4-Me₂N—C₆H₄ | 4-Me₂N—C₆H₄ | H | S | 5 | N(CH₂)₂O—(CH₂)₃CH₃ | O | CH | CH | — |
| 74 | 4-MeS—C₆H₄ | 4-MeS—C₆H₄ | H | S | 5 | N(CH₂)₂O—(CH₂)₃CH₃ | O | CH | CH | — |
| 75 | iPr | iPr | H | S | 5 | N(CH₂)₂O—(CH₂)₃CH₃ | O | CH | CH | — |
| 76 | Ph | Ph | H | CH₂ | 5 | S | NH | CH | CH | — |
| 77 | Ph | Ph | H | NMe | 5 | S | NH | CH | CH | — |
| 78 | 2-furanyl | 2-furanyl | H | S | 5 | N—C₇H₁₅ | O | CH | CH | — |
| 79 | 2-thienyl | 2-thienyl | H | S | 5 | N—C₇H₁₅ | O | CH | CH | — |
| 80 | 2-pyridyl | 2-pyridyl | H | S | 5 | N—C₇H₁₅ | O | CH | CH | — |
| 81 | c-C₆H₁₁ | c-C₆H₁₁ | H | S | 5 | N—C₇H₁₅ | O | CH | CH | — |
| 82 | 4-iPr—C₆H₄ | 4-iPr—C₆H₄ | H | S | 5 | N—C₇H₁₅ | O | CH | CH | — |
| 83 | Ph | H | H | S | 5 | N—C₇H₁₅ | O | CH | CH | — |
| 84 | H | H | H | S | 5 | N—C₇H₁₅ | O | CH | CH | — |
| 85 | Ph | Ph | H | S | 5 | N—Ph | O | CH | CH | — |
| 86 | Ph | Ph | H | S | 5 | N-(4-EtO—C₆H₄) | O | CH | CH | — |
| 87 | Ph | Ph | H | S | 5 | N-(4-MeS—C₆H₄) | O | CH | CH | — |
| 88 | Ph | Ph | H | S | 5 | N-(2,4-C₆H₃F₂) | O | CH | CH | — |
| 89 | Ph | Ph | H | S | 5 | N—CH₂Ph | O | CH | CH | — |
| 90 | Ph | Ph | H | S | 5 | N—(CH₂)₂—Ph | O | CH | CH | — |

*a)* ¹H NMR (CDCl₃): 7.40(4H, br d, J = 8.4Hz); 7.26-6.90(4H, m); 6.82(4H, d, J = 8.4Hz); 3.81(6H, br s); 3.59(2H, t, J = 6.6Hz); 3.46(2H, t, J = 7.0Hz); 3.18(2H, t, J = 6.9Hz); 1.80-1.45(8H, m); 1.36-1.10(8H, m); 0.88(3H, t, J = 6.6Hz).
*b)* ¹H NMR (CDCl₃): 10.84(1H, br s); 7.51(2H, d, J = 8.0Hz); 7.32-7.19(4H, m); 7.11(1H, t, J = 7.6Hz); 6.96(1H, t, J = 7.7Hz); 6.80(4H, d, J = 8.7Hz); 3.78(6H, s); 3.65(4H, br s); 3.60-3.49(6H, m); 3.34(3H, s); 3.00(2H, t, J = 7.0Hz); 1.78-1.64(4H, m); 1.47-1.37(2H, m).

TABLE 2

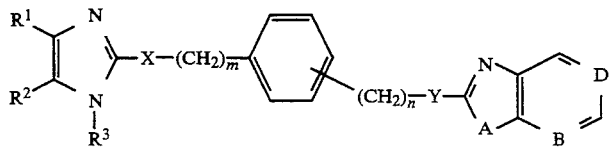

| Ex. | R¹ | R² | R³ | X | m | ring | n | Y | A | B | D | m.p. |
|---|---|---|---|---|---|---|---|---|---|---|---|---|
| 91 | Ph | Ph | H | S | 1 | meta | 1 | S | NH | CH | CH | — |
| 92 | 4-MeO—C₆H₄ | 4-MeO—C₆H₄ | H | S | 1 | meta | 1 | S | NH | CH | CH | — |
| 93 | 4-Me₂N—C₆H₄ | 4-Me₂N—C₆H₄ | H | S | 1 | meta | 1 | S | NH | CH | CH | — |
| 94 | 4-MeS—C₆H₄ | 4-MeS—C₆H₄ | H | S | 1 | meta | 1 | S | NH | CH | CH | — |
| 95 | iPr | iPr | H | S | 1 | meta | 1 | S | NH | CH | CH | — |
| 96 | Ph | Ph | H | S | 1 | meta | 1 | S | NH | N | CH | — |
| 97 | 4-MeO—C₆H₄ | 4-MeO—C₆H₄ | H | S | 1 | meta | 1 | S | NH | N | CH | — |
| 98 | 4-Me₂N—C₆H₄ | 4-Me₂N—C₆H₄ | H | S | 1 | meta | 1 | S | NH | N | CH | — |
| 99 | 4-MeS—C₆H₄ | 4-MeS—C₆H₄ | H | S | 1 | meta | 1 | S | NH | N | CH | — |
| 100 | iPr | iPr | H | S | 1 | meta | 1 | S | NH | N | CH | — |
| 101 | Ph | Ph | H | S | 1 | meta | 1 | S | NH | N | N | — |
| 102 | 4-MeO—C₆H₄ | 4-MeO—C₆H₄ | H | S | 1 | meta | 1 | S | NH | N | N | — |
| 103 | 4-Me₂N—C₆H₄ | 4-Me₂N—C₆H₄ | H | S | 1 | meta | 1 | S | NH | N | N | — |
| 104 | 4-MeS—C₆H₄ | 4-MeS—C₆H₄ | H | S | 1 | meta | 1 | S | NH | N | N | — |
| 105 | iPr | iPr | H | S | 1 | meta | 1 | S | NH | N | N | — |
| 106 | Ph | Ph | H | S | 1 | para | 2 | N—C₇H₁₅ | O | CH | CH | — |
| 107 | 4-MeO—C₆H₄ | 4-MeO—C₆H₄ | H | S | 1 | para | 2 | N—C₇H₁₅ | O | CH | CH | — |
| 108 | 4-Me₂N—C₆H₄ | 4-Me₂N—C₆H₄ | H | S | 1 | para | 2 | N—C₇H₁₅ | O | CH | CH | — |
| 109 | 4-MeS—C₆H₄ | 4-MeS—C₆H₄ | H | S | 1 | para | 2 | N—C₇H₁₅ | O | CH | CH | — |
| 110 | iPr | iPr | H | S | 1 | para | 2 | N—C₇H₁₅ | O | CH | CH | — |
| 111 | Ph | Ph | H | S | 1 | para | 2 | N—C₇H₁₅ | NH | CH | CH | — |
| 112 | 4-MeO—C₆H₄ | 4-MeO—C₆H₄ | H | S | 1 | para | 2 | N—C₇H₁₅ | NH | CH | CH | — |
| 113 | 4-Me₂N—C₆H₄ | 4-Me₂N—C₆H₄ | H | S | 1 | para | 2 | N—C₇H₁₅ | NH | CH | CH | — |
| 114 | 4-MeS—C₆H₄ | 4-MeS—C₆H₄ | H | S | 1 | para | 2 | N—C₇H₁₅ | NH | CH | CH | — |
| 115 | iPr | iPr | H | S | 1 | para | 2 | N—C₄H₁₅ | NH | CH | CH | — |
| 116 | Ph | Ph | H | S | 2 | para | 0 | N—C₇H₁₅ | S | CH | CH | — |
| 117 | 4-MeO—C₆H₄ | 4-MeO—C₆H₄ | H | S | 2 | para | 0 | N—C₇H₁₅ | S | CH | CH | — |
| 118 | 4-Me₂N—C₆H₄ | 4-Me₂N—C₆H₄ | H | S | 2 | para | 0 | N—C₇H₁₅ | S | CH | CH | — |
| 119 | 4-MeS—C₆H₄ | 4-MeS—C₆H₄ | H | S | 2 | para | 0 | N—C₇H₁₅ | S | CH | CH | — |
| 120 | iPr | iPr | H | S | 2 | para | 0 | N—C₇H₁₅ | S | CH | CH | — |
| 121 | Ph | Ph | H | S | 1 | meta | 1 | N(CH₂)₂O(CH₂)₂OMe | O | CH | CH | — |
| 122 | 4-MeO—C₆H₄ | 4-MeO—C₆H₄ | H | S | 1 | meta | 1 | N(CH₂)₂O(CH₂)₂OMe | O | CH | CH | — |
| 123 | 4-Me₂N—C₆H₄ | 4-Me₂N—C₆H₄ | H | S | 1 | meta | 1 | N(CH₂)₂O(CH₂)₂OMe | O | CH | CH | — |

TABLE 2-continued

| Ex. | R¹ | R² | R³ | X | m | ring | n | Y | A | B | D | m.p. |
|---|---|---|---|---|---|---|---|---|---|---|---|---|
| 124 | 4-MeS—C₆H₄ | 4-MeS—C₆H₄ | H | S | 1 | meta | 1 | N(CH₂)₂O(CH₂)₂OMe | O | CH | CH | — |
| 125 | iPr | iPr | H | S | 1 | meta | 1 | N(CH₂)₂O(CH₂)₂OMe | O | CH | CH | — |
| 126 | Ph | Ph | H | S | 1 | para | 1 | N(CH₂)₂O(CH₂)₂OMe | NH | CH | CH | — |
| 127 | 4-MeO—C₆H₄ | 4-MeO—C₆H₄ | H | S | 1 | para | 1 | N(CH₂)₂O(CH₂)₂OMe | NH | CH | CH | — |
| 128 | 4-Me₂N—C₆H₄ | 4-Me₂N—C₆H₄ | H | S | 1 | para | 1 | N(CH₂)₂O(CH₂)₂OMe | NH | CH | CH | — |
| 129 | 4-MeS—C₆H₄ | 4-MeS—C₆H₄ | H | S | 1 | para | 1 | N(CH₂)₂O(CH₂)₂OMe | NH | CH | CH | — |
| 130 | iPr | iPr | H | S | 1 | para | 1 | N(CH₂)₂O(CH₂)₂OMe | NH | CH | CH | — |
| 131 | Ph | Ph | H | S | 1 | para | 1 | N(CH₂)₂O(CH₂)₂OMe | S | CH | CH | — |
| 132 | 4-MeO—C₆H₄ | 4-MeO—C₆H₄ | H | S | 1 | para | 1 | N(CH₂)₂O(CH₂)₂OMe | S | CH | CH | — |
| 133 | 4-Me₂N—C₆H₄ | 4-Me₂N—C₆H₄ | H | S | 1 | para | 1 | N(CH₂)₂O(CH₂)₂OMe | S | CH | CH | — |
| 134 | 4-MeS—C₆H₄ | 4-MeS—C₆H₄ | H | S | 1 | para | 1 | N(CH₂)₂O(CH₂)₂OMe | S | CH | CH | — |
| 135 | iPr | iPr | H | S | 1 | para | 1 | N(CH₂)₂O(CH₂)₂OMe | S | CH | CH | — |
| 136 | Ph | Ph | H | S | 1 | para | 1 | N—C₇H₁₅ | NH | N | N | — |
| 137 | 4-MeO—C₆H₄ | 4-MeO—C₆H₄ | H | S | 1 | para | 1 | N—C₇H₁₅ | NH | N | N | — |
| 138 | 4-Me₂N—C₆H₄ | 4-Me₂N—C₆H₄ | H | S | 1 | para | 1 | N—C₇H₁₅ | NH | N | N | — |
| 139 | 4-MeS—C₆H₄ | 4-MeS—C₆H₄ | H | S | 1 | para | 1 | N—C₇H₁₅ | NH | N | N | — |
| 140 | iPr | iPr | H | S | 1 | para | 1 | N—C₇H₁₅ | NH | N | N | — |
| 141 | Ph | Ph | H | S | 1 | para | 1 | CH₂ | O | CH | CH | — |
| 142 | 4-MeO—C₆H₄ | 4-MeO—C₆H₄ | H | S | 1 | para | 1 | CH₂ | O | CH | CH | — |
| 143 | 4-Me₂N—C₆H₄ | 4-Me₂N—C₆H₄ | H | S | 1 | para | 1 | CH₂ | O | CH | CH | — |
| 144 | 4-MeS—C₆H₄ | 4-MeS—C₆H₄ | H | S | 1 | para | 1 | CH₂ | O | CH | CH | — |
| 145 | iPr | iPr | H | S | 1 | para | 1 | CH₂ | O | CH | CH | — |
| 146 | Ph | Ph | H | SO₂ | 1 | para | 1 | SO₂ | NH | CH | CH | — |
| 147 | 4-MeO—C₆H₄ | 4-MeO—C₆H₄ | H | SO₂ | 1 | para | 1 | SO₂ | NH | CH | CH | — |
| 148 | 4-Me₂N—C₆H₄ | 4-Me₂N—C₆H₄ | H | SO₂ | 1 | para | 1 | SO₂ | NH | CH | CH | — |
| 149 | 4-MeS—C₆H₄ | 4-MeS—C₆H₄ | H | SO₂ | 1 | para | 1 | SO₂ | NH | CH | CH | — |
| 150 | iPr | iPr | H | SO₂ | 1 | para | 1 | SO₂ | NH | CH | CH | — |
| 151 | Ph | Ph | H | S | 1 | meta | 1 | S | O | CH | CH | — |
| 152 | 4-MeO—C₆H₄ | 4-MeO—C₆H₄ | H | S | 1 | meta | 1 | S | O | CH | CH | 129–131 |
| 153 | 4-Me₂N—C₆H₄ | 4-Me₂N—C₆H₄ | H | S | 1 | meta | 1 | S | O | CH | CH | — |
| 154 | Ph | Ph | H | S | 1 | para | 1 | S | O | CH | CH | — |
| 155 | 4-MeO—C₆H₄ | 4-MeO—C₆H₄ | H | S | 1 | para | 1 | S | O | CH | CH | — |
| 156 | 4-Me₂N—C₆H₄ | 4-Me₂N—C₆H₄ | H | S | 1 | para | 1 | S | O | CH | CH | — |
| 157 | Ph | Ph | CH₃ | S | 1 | meta | 1 | S | O | CH | CH | — |
| 158 | 4-MeO—C₆H₄ | 4-MeO—C₆H₄ | CH₃ | S | 1 | meta | 1 | S | O | CH | CH | — |
| 159 | 4-Me₂N—C₆H₄ | 4-Me₂N—C₆H₄ | CH₃ | S | 1 | meta | 1 | S | O | CH | CH | — |
| 160 | 4-MeS—C₆H₄ | iPr | H | S | 1 | meta | 1 | S | O | CH | CH | — |
| 161 | Ph | Ph | H | S | 1 | meta | 1 | N(CH₂)₂O—C₄H₉ | O | CH | CH | — |
| 162 | 4-MeO—C₆H₄ | 4-MeO—C₆H₄ | H | S | 1 | meta | 1 | N(CH₂)₂O—C₄H₉ | O | CH | CH | — |
| 163 | 4-Me₂N—C₆H₄ | 4-Me₂N—C₆H₄ | H | S | 1 | meta | 1 | N(CH₂)₂O—C₄H₉ | O | CH | CH | — |
| 164 | 4-MeS—C₆H₄ | 4-MeS—C₆H₄ | H | S | 1 | meta | 1 | N(CH₂)₂O—C₄H₉ | O | CH | CH | — |
| 165 | iPr | iPr | H | S | 1 | meta | 1 | N(CH₂)₂O—C₄H₉ | O | CH | CH | — |
| 166 | Ph | Ph | H | CH₂ | 1 | meta | 1 | S | NH | CH | CH | — |
| 167 | Ph | Ph | H | NMe | 1 | meta | 1 | S | NH | CH | CH | — |
| 168 | 2-furanyl | 2-furanyl | H | S | 1 | meta | 1 | N—C₇H₁₅ | O | CH | CH | — |
| 169 | 2-thienyl | 2-thienyl | H | S | 1 | meta | 1 | N—C₇H₁₅ | O | CH | CH | — |
| 170 | 2-pyridyl | 2-pyridyl | H | S | 1 | meta | 1 | N—C₇H₁₅ | O | CH | CH | — |
| 171 | c-C₆H₁₁ | c-C₆H₁₁ | H | S | 1 | meta | 1 | N—C₇H₁₅ | O | CH | CH | — |
| 172 | 4-iPr—C₆H₄ | 4-iPr—C₆H₄ | H | S | 1 | meta | 1 | N—C₇H₁₅ | O | CH | CH | — |
| 173 | Ph | H | H | S | 1 | meta | 1 | N—C₇H₁₅ | O | CH | CH | — |
| 174 | H | H | H | S | 1 | meta | 1 | N—C₇H₁₅ | O | CH | CH | — |
| 175 | Ph | Ph | H | S | 1 | meta | 1 | N—Ph | O | CH | CH | — |
| 176 | Ph | Ph | H | S | 1 | meta | 1 | N-(4-EtO—C₆H₄) | O | CH | CH | — |
| 177 | Ph | Ph | H | S | 1 | meta | 1 | N-(4-MeS—C₆H₄) | O | CH | CH | — |
| 178 | Ph | Ph | H | S | 1 | meta | 1 | N-(2,4-C₆H₃F₂) | O | CH | CH | — |
| 179 | Ph | Ph | H | S | 1 | meta | 1 | N—CH₂Ph | O | CH | CH | — |
| 180 | Ph | Ph | H | S | 1 | meta | 1 | N—(CH₂)₂—Ph | O | CH | CH | — |

TABLE 3

| Ex. | R¹ | R² | R³ | X | m + n + 1 | R⁵ | B | D | E | m.p. |
|---|---|---|---|---|---|---|---|---|---|---|
| 181 | Ph | Ph | H | S | 5 | iPr | N | CH | CH | 76–79 |
| 182 | 4-MeO—C₆H₄ | 4-MeO—C₆H₄ | H | S | 5 | iPr | N | CH | CH | 78–80 |
| 183 | 4-Me₂N—C₆H₄ | 4-Me₂N—C₆H₄ | H | S | 5 | iPr | N | CH | CH | 110–112 |
| 184 | 4-MeS—C₆H₄ | 4-MeS—C₆H₄ | H | S | 5 | iPr | N | CH | CH | — |
| 185 | iPr | iPr | H | S | 5 | iPr | N | CH | CH | — |
| 186 | Ph | Ph | H | S | 5 | CH₃ | N | CH | CH | — |
| 187 | 4-MeO—C₆H₄ | 4-MeO—C₆H₄ | H | S | 5 | CH₃ | N | CH | CH | — |
| 188 | 4-Me₂N—C₆H₄ | 4-Me₂N—C₆H₄ | H | S | 5 | CH₃ | N | CH | CH | — |
| 189 | 4-MeS—C₆H₄ | 4-MeS—C₆H₄ | H | S | 5 | CH₃ | N | CH | CH | — |
| 190 | iPr | iPr | H | S | 5 | CH₃ | N | CH | CH | — |
| 191 | Ph | Ph | H | S | 5 | SCH₃ | N | CH | CH | — |
| 192 | 4-MeO—C₆H₄ | 4-MeO—C₆H₄ | H | S | 5 | SCH₃ | N | CH | CH | 60–65 |
| 193 | 4-Me₂N—C₆H₄ | 4-Me₂N—C₆H₄ | H | S | 5 | SCH₃ | N | CH | CH | — |
| 194 | 4-MeS—C₆H₄ | 4-MeS—C₆H₄ | H | S | 5 | SCH₃ | N | CH | CH | — |
| 195 | iPr | iPr | H | S | 5 | SCH₃ | N | CH | CH | — |
| 196 | Ph | Ph | H | S | 5 | NH—C₆H₅ | N | CH | CH | — |
| 197 | 4-MeO—C₆H₄ | 4-MeO—C₆H₄ | H | S | 5 | NH—C₆H₅ | N | CH | CH | 125–126 |
| 198 | 4-Me₂N—C₆H₄ | 4-Me₂N—C₆H₄ | H | S | 5 | NH—C₆H₅ | N | CH | CH | — |
| 199 | 4-MeS—C₆H₄ | 4-MeS—C₆H₄ | H | S | 5 | NH—C₆H₅ | N | CH | CH | — |
| 200 | iPr | iPr | H | S | 5 | NH—C₆H₅ | N | CH | CH | — |
| 201 | Ph | Ph | H | S | 5 | H | N | N | N | — |
| 202 | 4-MeO—C₆H₄ | 4-MeO—C₆H₄ | H | S | 5 | H | N | N | N | — |
| 203 | 4-Me₂N—C₆H₄ | 4-Me₂N—C₆H₄ | H | S | 5 | H | N | N | N | — |
| 204 | 4-MeS—C₆H₄ | 4-MeS—C₆H₄ | H | S | 5 | H | N | N | N | — |
| 205 | iPr | iPr | H | S | 5 | H | N | N | N | — |
| 206 | Ph | Ph | H | S | 5 | SCH₃ | N | N | N | — |
| 207 | 4-MeO—C₆H₄ | 4-MeO—C₆H₄ | H | S | 5 | SCH₃ | N | N | N | — |
| 208 | 4-Me₂N—C₆H₄ | 4-Me₂N—C₆H₄ | H | S | 5 | SCH₃ | N | N | N | — |
| 209 | 4-MeS—C₆H₄ | 4-MeS—C₆H₄ | H | S | 5 | SCH₃ | N | N | N | — |
| 210 | iPr | iPr | H | S | 5 | SCH₃ | N | N | N | — |
| 211 | Ph | Ph | H | S | 5 | H | N | CH | N | — |
| 212 | 4-MeO—C₆H₄ | 4-MeO—C₆H₄ | H | S | 5 | H | N | CH | N | — |
| 213 | 4-Me₂N—C₆H₄ | 4-Me₂N—C₆H₄ | H | S | 5 | H | N | CH | N | — |
| 214 | 4-MeS—C₆H₄ | 4-MeS—C₆H₄ | H | S | 5 | H | N | CH | N | — |
| 215 | iPr | iPr | H | S | 5 | H | N | CH | N | — |
| 216 | Ph | Ph | H | S | 5 | SCH₃ | N | CH | N | — |
| 217 | 4-MeO—C₆H₄ | 4-MeO—C₆H₄ | H | S | 5 | SCH₃ | N | CH | N | — |
| 218 | 4-Me₂N—C₆H₄ | 4-Me₂N—C₆H₄ | H | S | 5 | SCH₃ | N | CH | N | — |
| 219 | 4-MeS—C₆H₄ | 4-MeS—C₆H₄ | H | S | 5 | SCH₃ | N | CH | N | — |
| 220 | iPr | iPr | H | S | 5 | SCH₃ | N | CH | N | — |
| 221 | Ph | Ph | H | S | 5 | CH₃ | CH | CH | CH | — |
| 222 | 4-MeO—C₆H₄ | 4-MeO—C₆H₄ | H | S | 5 | CH₃ | CH | CH | CH | — |
| 223 | 4-Me₂N—C₆H₄ | 4-Me₂N—C₆H₄ | H | S | 5 | CH₃ | CH | CH | CH | — |
| 224 | 4-MeS—C₆H₄ | 4-MeS—C₆H₄ | H | S | 5 | CH₃ | CH | CH | CH | — |
| 225 | iPr | iPr | H | S | 5 | CH₃ | CH | CH | CH | — |
| 226 | Ph | Ph | H | S | 3 | iPr | N | CH | CH | — |
| 227 | 4-MeO—C₆H₄ | 4-MeO—C₆H₄ | H | S | 3 | iPr | N | CH | CH | — |
| 228 | 4-Me₂N—C₆H₄ | 4-Me₂N—C₆H₄ | H | S | 3 | iPr | N | CH | CH | — |
| 229 | 4-MeS—C₆H₄ | 4-MeS—C₆H₄ | H | S | 3 | iPr | N | CH | CH | — |
| 230 | iPr | iPr | H | S | 3 | iPr | N | CH | CH | — |
| 231 | Ph | Ph | H | S | 3 | CH₃ | N | CH | CH | — |
| 232 | 4-MeO—C₆H₄ | 4-MeO—C₆H₄ | H | S | 3 | CH₃ | N | CH | CH | — |
| 233 | 4-Me₂N—C₆H₄ | 4-Me₂N—C₆H₄ | H | S | 3 | CH₃ | N | CH | CH | — |
| 234 | 4-MeS—C₆H₄ | 4-MeS—C₆H₄ | H | S | 3 | CH₃ | N | CH | CH | — |
| 235 | iPr | iPr | H | S | 3 | CH₃ | N | CH | CH | — |
| 236 | Ph | Ph | H | S | 3 | SCH₃ | N | CH | CH | — |
| 237 | 4-MeO—C₆H₄ | 4-MeO—C₆H₄ | H | S | 3 | SCH₃ | N | CH | CH | — |
| 238 | 4-Me₂N—C₆H₄ | 4-Me₂N—C₆H₄ | H | S | 3 | SCH₃ | N | CH | CH | — |
| 239 | 4-MeS—C₆H₄ | 4-MeS—C₆H₄ | H | S | 3 | SCH₃ | N | CH | CH | — |
| 240 | iPr | iPr | H | S | 3 | SCH₃ | N | CH | CH | — |
| 241 | Ph | Ph | H | S | 3 | NH—C₆H₅ | N | CH | CH | — |
| 242 | 4-MeO—C₆H₄ | 4-MeO—C₆H₄ | H | S | 3 | NH—C₆H₅ | N | CH | CH | — |
| 243 | 4-Me₂N—C₆H₄ | 4-Me₂N—C₆H₄ | H | S | 3 | NH—C₆H₅ | N | CH | CH | — |
| 244 | 4-MeS—C₆H₄ | 4-MeS—C₆H₄ | H | S | 3 | NH—C₆H₅ | N | CH | CH | — |
| 245 | iPr | iPr | H | S | 3 | NH—C₆H₅ | N | CH | CH | — |
| 246 | Ph | Ph | H | S | 8 | iPr | N | CH | CH | — |
| 247 | 4-MeO—C₆H₄ | 4-MeO—C₆H₄ | H | S | 8 | iPr | N | CH | CH | — |
| 248 | 4-Me₂N—C₆H₄ | 4-Me₂N—C₆H₄ | H | S | 8 | iPr | N | CH | CH | — |
| 249 | 4-MeS—C₆H₄ | 4-MeS—C₆H₄ | H | S | 8 | iPr | N | CH | CH | — |
| 250 | iPr | iPr | H | S | 8 | iPr | N | CH | CH | — |
| 251 | Ph | Ph | H | S | 8 | CH₃ | N | CH | CH | — |

TABLE 3-continued

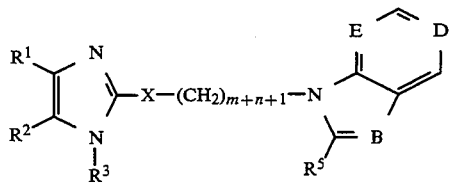

| Ex. | R¹ | R² | R³ | X | m + n + 1 | R⁵ | B | D | E | m.p. |
|---|---|---|---|---|---|---|---|---|---|---|
| 252 | 4-MeO—C₆H₄ | 4-MeO—C₆H₄ | H | S | 8 | CH₃ | N | CH | CH | — |
| 253 | 4-Me₂N—C₆H₄ | 4-Me₂N—C₆H₄ | H | S | 8 | CH₃ | N | CH | CH | — |
| 254 | 4-MeS—C₆H₄ | 4-MeS—C₆H₄ | H | S | 8 | CH₃ | N | CH | CH | — |
| 255 | iPr | iPr | H | S | 8 | CH₃ | N | CH | CH | — |
| 256 | Ph | Ph | H | S | 8 | SCH₃ | N | CH | CH | — |
| 257 | 4-MeO—C₆H₄ | 4-MeO—C₆H₄ | H | S | 8 | SCH₃ | N | CH | CH | — |
| 258 | 4-Me₂N—C₆H₄ | 4-Me₂N—C₆H₄ | H | S | 8 | SCH₃ | N | CH | CH | — |
| 259 | 4-MeS—C₆H₄ | 4-MeS—C₆H₄ | H | S | 8 | SCH₃ | N | CH | CH | — |
| 260 | iPr | iPr | H | S | 8 | SCH₃ | N | CH | CH | — |
| 261 | Ph | Ph | H | S | 8 | NH—C₆H₅ | N | CH | CH | — |
| 262 | 4-MeO—C₆H₄ | 4-MeO—C₆H₄ | H | S | 8 | NH—C₆H₅ | N | CH | CH | — |
| 263 | 4-Me₂N—C₆H₄ | 4-Me₂N—C₆H₄ | H | S | 8 | NH—C₆H₅ | N | CH | CH | — |
| 264 | 4-MeS—C₆H₄ | 4-MeS—C₆H₄ | H | S | 8 | NH—C₆H₅ | N | CH | CH | — |
| 265 | iPr | iPr | H | S | 8 | NH—C₆H₅ | N | CH | CH | — |
| 266 | Ph | Ph | H | SO₂ | 5 | iPr | N | CH | CH | — |
| 267 | 4-MeO—C₆H₄ | 4-MeO—C₆H₄ | H | SO₂ | 5 | iPr | N | CH | CH | — |
| 268 | 4-Me₂N—C₆H₄ | 4-Me₂N—C₆H₄ | H | SO₂ | 5 | iPr | N | CH | CH | — |
| 269 | 4-MeS—C₆₄ | 4-MeS—C₆₄ | H | SO₂ | 5 | iPr | N | CH | CH | — |
| 270 | iPr | iPr | H | SO₂ | 5 | iPr | N | CH | CH | — |
| 271 | Ph | Ph | CH₃ | NMe | 5 | iPr | N | CH | CH | — |
| 272 | 4-MeO—C₆H₄ | 4-MeO—C₆H₄ | CH₃ | NMe | 5 | iPr | N | CH | CH | — |
| 273 | 4-Me₂N—C₆H₄ | 4-Me₂N—C₆H₄ | CH₃ | NMe | 5 | iPr | N | CH | CH | — |
| 274 | 4-MeS—C₆H₄ | 4-MeS—C₆H₄ | CH₃ | NMe | 5 | iPr | N | CH | CH | — |
| 275 | iPr | iPr | CH₃ | NMe | 5 | iPr | N | CH | CH | — |
| 276 | Ph | Ph | H | S | 5 | NMe₂ | N | CH | CH | — |
| 277 | 4-Cl—C₆H₄ | 4-Cl—C₆H₄ | H | S | 5 | iPr | N | CH | CH | — |
| 278 | 4-Me₂N—C₆H₄ | 4-Me₂N—C₆H₄ | H | CH₂ | 5 | iPr | N | CH | CH | — |
| 279 | 4-MeS—C₆H₄ | iPr | H | S | 5 | iPr | N | CH | CH | — |
| 280 | 4-MeS—C₆H₄ | c-C₆H₁₁ | H | S | 5 | iPr | N | CH | CH | — |

TABLE 4

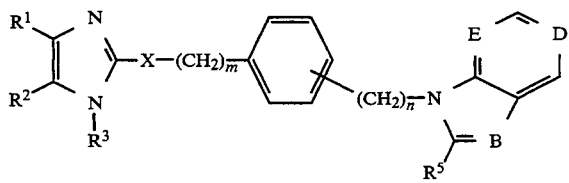

| Ex. | R¹ | R² | R³ | X | m | ring | n | R⁵ | B | D | E |
|---|---|---|---|---|---|---|---|---|---|---|---|
| 281 | Ph | Ph | H | S | 1 | para | 1 | iPr | N | CH | CH |
| 282 | 4-MeO—C₆H₄ | 4-MeO—C₆H₄ | H | S | 1 | para | 1 | para | N | CH | CH |
| 283 | 4-Me₂N—C₆H₄ | 4-Me₂N—C₆H₄ | H | S | 1 | para | 1 | iPr | N | CH | CH |
| 284 | 4-MeS—C₆H₄ | 4-MeS—C₆H₄ | H | S | 1 | para | 1 | iPr | N | CH | CH |
| 285 | iPr | iPr | H | S | 1 | para | 1 | iPr | N | CH | CH |
| 286 | Ph | Ph | H | S | 1 | para | 1 | CH₃ | N | CH | CH |
| 287 | 4-MeO—C₆H₄ | 4-MeO—C₆H₄ | H | S | 1 | para | 1 | CH₃ | N | CH | CH |
| 288 | 4-Me₂N—C₆H₄ | 4-Me₂N—C₆H₄ | H | S | 1 | para | 1 | CH₃ | N | CH | CH |
| 289 | 4-MeS—C₆H₄ | 4-MeS—C₆H₄ | H | S | 1 | para | 1 | CH₃ | N | CH | CH |
| 290 | iPr | iPr | H | S | 1 | para | 1 | CH₃ | N | CH | CH |
| 291 | Ph | Ph | H | S | 1 | meta | 1 | SCH₃ | N | CH | CH |
| 292 | 4-MeO—C₆H₄ | 4-MeO—C₆H₄ | H | S | 1 | meta | 1 | SCH₃ | N | CH | CH |
| 293 | 4-Me₂N—C₆H₄ | 4-Me₂N—C₆H₄ | H | S | 1 | meta | 1 | SCH₃ | N | CH | CH |
| 294 | 4-MeS—C₆H₄ | 4-MeS—C₆H₄ | H | S | 1 | meta | 1 | SCH₃ | N | CH | CH |
| 295 | iPr | iPr | H | S | 1 | meta | 1 | SCH₃ | N | CH | CH |
| 296 | Ph | Ph | H | S | 1 | meta | 1 | NH—C₆H₅ | N | CH | CH |
| 297 | 4-MeO— | 4-MeO— | H | S | 1 | meta | 1 | NH— | N | CH | CH |

TABLE 4-continued

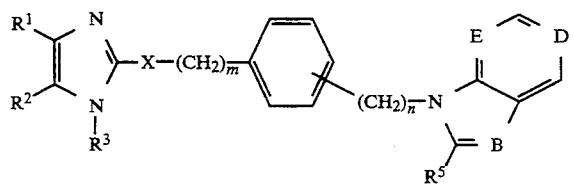

| Ex. | R¹ | R² | R³ | X | m | ring | n | R⁵ | B | D | E |
|---|---|---|---|---|---|---|---|---|---|---|---|
| 298 | 4-Me₂N—C₆H₄ | 4-Me₂N—C₆H₄ | H | S | 1 | meta | 1 | NH—C₆H₅ | N | CH | CH |
| 299 | 4-MeS—C₆H₄ | 4-MeS—C₆H₄ | H | S | 1 | meta | 1 | NH—C₆H₅ | N | CH | CH |
| 300 | iPr | iPr | H | S | 1 | meta | 1 | NH—C₆H₅ | N | CH | CH |
| 301 | Ph | Ph | H | S | 1 | para | 1 | H | N | N | N |
| 302 | 4-MeO—C₆H₄ | 4-MeO—C₆H₄ | H | S | 1 | para | 1 | H | N | N | N |
| 303 | 4-Me₂N—C₆H₄ | 4-Me₂—C₆H₄ | H | S | 1 | para | 1 | H | N | N | N |
| 304 | 4-MeS—C₆H₄ | 4-MeS—C₆H₄ | H | S | 1 | para | 1 | H | N | N | N |
| 305 | iPr | iPr | H | S | 1 | para | 1 | H | N | N | N |
| 306 | Ph | Ph | H | S | 1 | para | 1 | SCH₃ | N | N | N |
| 307 | 4-MeO—C₆H₄ | 4-MeO—C₆H₄ | H | S | 1 | para | 1 | SCH₃ | N | N | N |
| 308 | 4-Me₂N—C₆H₄ | 4-Me₂N—C₆H₄ | H | S | 1 | para | 1 | SCH₃ | N | N | N |
| 309 | 4-MeS—C₆H₄ | 4-MeS—C₆H₄ | H | S | 1 | para | 1 | SCH₃ | N | N | N |
| 310 | iPr | iPr | H | S | 1 | para | 1 | SCH₃ | N | N | N |
| 311 | Ph | Ph | H | S | 1 | meta | 1 | H | N | CH | N |
| 312 | 4-MeO—C₆H₄ | 4-MeO—C₆H₄ | H | S | 1 | meta | 1 | H | N | CH | N |
| 313 | 4-Me₂N—C₆H₄ | 4-Me₂N—C₆H₄ | H | S | 1 | meta | 1 | H | N | CH | N |
| 314 | 4-MeS—C₆H₄ | 4-MeS—C₆H₄ | H | S | 1 | meta | 1 | H | N | CH | N |
| 315 | iPr | iPr | H | S | 1 | meta | 1 | H | N | CH | N |
| 316 | Ph | Ph | H | S | 1 | meta | 1 | SCH₃ | N | CH | N |
| 317 | 4-MeO—C₆H₄ | 4-MeO—C₆H₄ | H | S | 1 | meta | 1 | SCH₃ | N | CH | N |
| 318 | 4-Me₂N—C₆H₄ | 4-Me₂N—C₆H₄ | H | S | 1 | meta | 1 | SCH₃ | N | CH | N |
| 319 | 4-MeS—C₆H₄ | 4-MeS—C₆H₄ | H | S | 1 | meta | 1 | SCH₃ | N | CH | N |
| 320 | iPr | iPr | H | S | 1 | meta | 1 | SCH₃ | N | CH | N |
| 321 | Ph | Ph | H | S | 1 | meta | 1 | CH₃ | CH | CH | CH |
| 322 | 4-MeO—C₆H₄ | 4-MeO—C₆H₄ | H | S | 1 | meta | 1 | CH₃ | CH | CH | CH |
| 323 | 4-Me₂N—C₆H₄ | 4-Me₂N—C₆H₄ | H | S | 1 | meta | 1 | CH₃ | CH | CH | CH |
| 324 | 4-MeS—C₆H₄ | 4-MeS—C₆H₄ | H | S | 1 | meta | 1 | CH₃ | CH | CH | CH |
| 325 | iPr | iPr | H | S | 1 | meta | 1 | CH₃ | CH | CH | CH |
| 326 | Ph | Ph | H | S | 1 | meta | 1 | iPr | N | CH | CH |
| 327 | 4-MeO—C₆H₄ | 4-MeO—C₆H₄ | H | S | 2 | meta | 1 | iPr | N | CH | CH |
| 328 | 4-Me₂N—C₆H₄ | 4-Me₂N—C₆H₄ | H | S | 2 | meta | 1 | iPr | N | CH | CH |
| 329 | 4-MeS—C₆H₄ | 4-MeS—C₆H₄ | H | S | 2 | meta | 1 | iPr | N | CH | CH |
| 330 | iPr | iPr | H | S | 2 | meta | 1 | iPr | N | CH | CH |
| 331 | Ph | Ph | H | S | 2 | meta | 1 | CH₃ | N | CH | CH |
| 332 | 4-MeO—C₆H₄ | 4-MeO—C₆H₄ | H | S | 2 | meta | 1 | CH₃ | N | CH | CH |
| 333 | 4-Me₂N—C₆H₄ | 4-Me₂N—C₆H₄ | H | S | 2 | meta | 1 | CH₃ | N | CH | CH |
| 334 | 4-MeS—C₆H₄ | 4-MeS—C₆H₄ | H | S | 2 | meta | 1 | CH₃ | N | CH | CH |
| 335 | iPr | iPr | H | S | 2 | meta | 1 | CH₃ | N | CH | CH |
| 336 | Ph | Ph | H | S | 2 | para | 1 | SCH₃ | N | CH | CH |
| 337 | 4-MeO—C₆H₄ | 4-MeO—C₆H₄ | H | S | 2 | para | 1 | SCH₃ | N | CH | CH |
| 338 | 4-Me₂N—C₆H₄ | 4-Me₂N—C₆H₄ | H | S | 2 | para | 1 | SCH₃ | N | CH | CH |
| 339 | 4-MeS—C₆H₄ | 4-MeS—C₆H₄ | H | S | 2 | para | 1 | SCH₃ | N | CH | CH |
| 340 | iPr | iPr | H | S | 2 | para | 1 | SCH₃ | N | CH | CH |

TABLE 4-continued

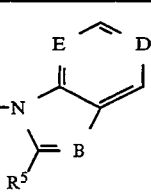

| Ex. | R¹ | R² | R³ | X | m | ring | n | R⁵ | B | D | E |
|---|---|---|---|---|---|---|---|---|---|---|---|
| 341 | Ph | Ph | H | S | 2 | para | 1 | NH—C₆H₅ | N | CH | CH |
| 342 | 4-MeO—C₆H₄ | 4-MeO—C₆H₄ | H | S | 2 | para | 1 | NH—C₆H₅ | N | CH | CH |
| 343 | 4-Me₂N—C₆H₄ | 4-Me₂N—C₆H₄ | H | S | 2 | para | 1 | NH—C₆H₅ | N | CH | CH |
| 344 | 4-MeS—C₆H₄ | 4-MeS—C₆H₄ | H | S | 2 | para | 1 | NH—C₆H₅ | N | CH | CH |
| 345 | iPr | iPr | H | S | 2 | para | 1 | NH—C₆H₅ | N | CH | CH |
| 346 | Ph | Ph | H | S | 1 | ortho | 1 | iPr | N | CH | CH |
| 347 | 4-MeO—C₆H₄ | 4-MeO—C₆H₄ | H | S | 1 | ortho | 1 | iPr | N | CH | CH |
| 348 | 4-Me₂N—C₆H₄ | 4-Me₂N—C₆H₄ | H | S | 1 | ortho | 1 | iPr | N | CH | CH |
| 349 | 4-MeS—C₆H₄ | 4-MeS—C₆H₄ | H | S | 1 | ortho | 1 | iPr | N | CH | CH |
| 350 | iPr | iPr | H | S | 1 | ortho | 1 | iPr | N | CH | CH |
| 351 | Ph | Ph | H | S | 1 | ortho | 1 | CH₃ | N | CH | CH |
| 352 | 4-MeO—C₆H₄ | 4-MeO—C₆H₄ | H | S | 1 | ortho | 1 | CH₃ | N | CH | CH |
| 353 | 4-Me₂N—C₆H₄ | 4-Me₂N—C₆H₄ | H | S | 1 | ortho | 1 | CH₃ | N | CH | CH |
| 354 | 4-MeS—C₆H₄ | 4-MeS—C₆H₄ | H | S | 1 | ortho | 1 | CH₃ | N | CH | CH |
| 355 | iPr | iPr | H | S | 1 | ortho | 1 | CH₃ | N | CH | CH |
| 356 | Ph | Ph | H | S | 1 | ortho | 1 | SCH₃ | N | CH | CH |
| 357 | 4-MeO—C₆H₄ | 4-MeO—C₆H₄ | H | S | 1 | ortho | 1 | SCH₃ | N | CH | CH |
| 358 | 4-Me₂N—C₆H₄ | 4-Me₂N—C₆H₄ | H | S | 1 | ortho | 1 | SCH₃ | N | CH | CH |
| 359 | 4-MeS—C₆H₄ | 4-MeS—C₆H₄ | H | S | 1 | ortho | 1 | SCH₃ | N | CH | CH |
| 360 | iPr | iPr | H | S | 1 | ortho | 1 | SCH₃ | N | CH | CH |
| 361 | Ph | Ph | H | S | 1 | ortho | 1 | NH—C₆H₅ | N | CH | CH |
| 362 | 4-MeO—C₆H₄ | 4-MeO—C₆H₄ | H | S | 1 | ortho | 1 | NH—C₆H₅ | N | CH | CH |
| 363 | 4-Me₂N—C₆H₄ | 4-Me₂N—C₆H₄ | H | S | 1 | ortho | 1 | NH—C₆H₅ | N | CH | CH |
| 364 | 4-MeS—C₆H₄ | 4-MeS—C₆H₄ | H | S | 1 | ortho | 1 | NH—C₆H₅ | N | CH | CH |
| 365 | iPr | iPr | H | S | 1 | ortho | 1 | NH—C₆H₅ | N | CH | CH |
| 366 | Ph | Ph | H | SO₂ | 1 | para | 1 | iPr | N | CH | CH |
| 367 | 4-MeO—C₆H₄ | 4-MeO—C₆H₄ | H | SO₂ | 1 | para | 1 | iPr | N | CH | CH |
| 368 | 4-Me₂N—C₆H₄ | 4-Me₂N—C₆H₄ | H | SO₂ | 1 | para | 1 | iPr | N | CH | CH |
| 369 | 4-MeS—C₆H₄ | 4-MeS—C₆H₄ | H | SO₂ | 1 | para | 1 | iPr | N | CH | CH |
| 370 | iPr | iPr | H | SO₂ | 1 | para | 1 | iPr | N | CH | CH |
| 371 | Ph | Ph | CH₃ | NMe | 1 | para | 1 | iPr | N | CH | CH |
| 372 | 4-MeO—C₆H₄ | 4-MeO—C₆H₄ | CH₃ | NMe | 1 | para | 1 | iPr | N | CH | CH |
| 373 | 4-Me₂N—C₆H₄ | 4-Me₂N—C₆H₄ | CH₃ | NMe | 1 | para | 1 | iPr | N | CH | CH |
| 374 | 4-MeS—C₆H₄ | 4-MeS—C₆H₄ | CH₃ | NMe | 1 | para | 1 | iPr | N | CH | CH |
| 375 | iPr | iPr | CH₃ | NMe | 1 | para | 1 | iPr | N | CH | CH |
| 376 | Ph | Ph | H | S | 1 | para | 1 | NMe₂ | N | CH | CH |
| 377 | 4-Cl—C₆H₄ | 4-Cl—C₆H₄ | H | S | 1 | para | 1 | iPr | N | CH | CH |
| 378 | 4-Me₂N—C₆H₄ | 4-Me₂N—C₆H₄ | H | CH₂ | 1 | para | 1 | iPr | N | CH | CH |
| 379 | 4-MeS—C₆H₄ | iPr | H | S | 1 | para | 1 | iPr | N | CH | CH |
| 380 | 4-MeS—C₆H₄ | c-C₆H₁₁ | H | S | 1 | para | 1 | iPr | N | CH | CH |

TABLE 5

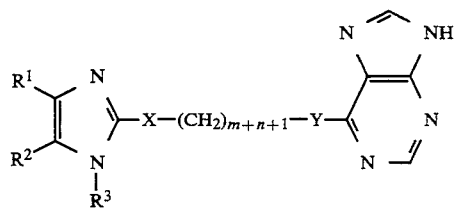

| Ex. | R¹ | R² | R³ | X | m + n + 1 | Y | m.p. |
|---|---|---|---|---|---|---|---|
| 381 | Ph | Ph | H | S | 5 | N—$C_7H_{15}$ | 58–60 |
| 382 | 4-MeO—$C_6H_4$ | 4-MeO—$C_6H_4$ | H | S | 5 | N—$C_7H_{15}$ | — |
| 383 | 4-$Me_2$N—$C_6H_4$ | 4-$Me_2$N—$C_6H_4$ | H | S | 5 | N—$C_7H_{15}$ | — |
| 384 | 4-MeS—$C_6H_4$ | 4-MeS—$C_6H_4$ | H | S | 5 | N—$C_7H_{15}$ | — |
| 385 | iPr | iPr | H | S | 5 | N—$C_7H_{15}$ | — |
| 386 | Ph | Ph | H | S | 5 | N—$(CH_2)_2OC_4H_9$ | — |
| 387 | 4-MeO—$C_6H_4$ | 4-MeO—$C_6H_4$ | H | S | 5 | N—$(CH_2)_2OC_4H_9$ | — |
| 388 | 4-$Me_2$N—$C_6H_4$ | 4-$Me_2$N—$C_6H_4$ | H | S | 5 | N—$(CH_2)_2OC_4H_9$ | — |
| 389 | 4-MeS—$C_6H_4$ | 4-MeS—$C_6H_4$ | H | S | 5 | N—$(CH_2)_2OC_4H_9$ | — |
| 390 | iPr | iPr | H | S | 5 | N—$(CH_2)_2OC_4H_9$ | — |
| 391 | Ph | Ph | H | S | 5 | N—$(CH_2)_2O$—$(CH_2)_2OCH_3$ | — |
| 392 | 4-MeO—$C_6H_4$ | 4-MeO—$C_6H_4$ | H | S | 5 | N—$(CH_2)_2O$—$(CH_2)_2OCH_3$ | — |
| 393 | 4-$Me_2$N—$C_6H_4$ | 4-$Me_2$N—$C_6H_4$ | H | S | 5 | N—$(CH_2)_2O$—$(CH_2)_2OCH_3$ | — |
| 394 | 4-MeS—$C_6H_4$ | 4-MeS—$C_6H_4$ | H | S | 5 | N—$(CH_2)_2O$—$(CH_2)_2OCH_3$ | — |
| 395 | iPr | iPr | H | S | 5 | N—$(CH_2)_2O$—$(CH_2)_2OCH_3$ | — |
| 396 | Ph | Ph | H | S | 5 | S | 167–168 |
| 397 | 4-MeO—$C_6H_4$ | 4-MeO—$C_6H_4$ | H | S | 5 | S | — |
| 398 | 4-$Me_2$N—$C_6H_4$ | 4-$Me_2$N—$C_6H_4$ | H | S | 5 | S | — |
| 399 | 4-MeS—$C_6H_4$ | 4-MeS—$C_6H_4$ | H | S | 5 | S | — |
| 400 | iPr | iPr | H | S | 5 | S | — |
| 401 | Ph | Ph | H | S | 3 | N—$C_7H_{15}$ | — |
| 402 | 4-MeO—$C_6H_4$ | 4-MeO—$C_6H_4$ | H | S | 3 | N—$C_7H_{15}$ | — |
| 403 | 4-$Me_2$N—$C_6H_4$ | 4-$Me_2$N—$C_6H_4$ | H | S | 3 | N—$C_7H_{15}$ | — |
| 404 | 4-MeS—$C_6H_4$ | 4-MeS—$C_6H_4$ | H | S | 3 | N—$C_7H_{15}$ | — |
| 405 | iPr | iPr | H | S | 3 | N—$C_7H_{15}$ | — |
| 406 | Ph | Ph | H | S | 3 | N—$(CH_2)_2OC_4H_9$ | — |
| 407 | 4-MeO—$C_6H_4$ | 4-MeO—$C_6H_4$ | H | S | 3 | N—$(CH_2)_2OC_4H_9$ | — |
| 408 | 4-$Me_2$N—$C_6H_4$ | 4-$Me_2$N—$C_6H_4$ | H | S | 3 | N—$(CH_2)_2OC_4H_9$ | — |
| 409 | 4-MeS—$C_6H_4$ | 4-MeS—$C_6H_4$ | H | S | 3 | N—$(CH_2)_2OC_4H_9$ | — |
| 410 | iPr | iPr | H | S | 3 | N—$(CH_2)_2OC_4H_9$ | — |
| 411 | Ph | Ph | H | S | 3 | N—$(CH_2)_2O$—$(CH_2)_2OCH_3$ | — |
| 412 | 4-MeO—$C_6H_4$ | 4-MeO—$C_6H_4$ | H | S | 3 | N—$(CH_2)_2O$—$(CH_2)_2OCH_3$ | — |
| 413 | 4-$Me_2$N—$C_6H_4$ | 4-$Me_2$N—$C_6H_4$ | H | S | 3 | N—$(CH_2)_2O$—$(CH_2)_2OCH_3$ | — |
| 414 | 4-MeS—$C_6H_4$ | 4-MeS—$C_6H_4$ | H | S | 3 | N—$(CH_2)_2O$—$(CH_2)_2OCH_3$ | — |
| 415 | iPr | iPr | H | S | 3 | N—$(CH_2)_2O$—$(CH_2)_2OCH_3$ | — |
| 416 | Ph | Ph | H | S | 3 | S | — |
| 417 | 4-MeO—$C_6H_4$ | 4-MeO—$C_6H_4$ | H | S | 3 | S | — |
| 418 | 4-$Me_2$N—$C_6H_4$ | 4-$Me_2$N—$C_6H_4$ | H | S | 3 | S | — |
| 419 | 4-MeS—$C_6H_4$ | 4-MeS—$C_6H_4$ | H | S | 3 | S | — |
| 420 | iPr | iPr | H | S | 3 | S | — |
| 421 | Ph | Ph | H | S | 8 | N—$C_7H_{15}$ | — |
| 422 | 4-MeO—$C_6H_4$ | 4-MeO—$C_6H_4$ | H | S | 8 | N—$C_7H_{15}$ | — |
| 423 | 4-$Me_2$N—$C_6H_4$ | 4-$Me_2$N—$C_6H_4$ | H | S | 8 | N—$C_7H_{15}$ | — |
| 424 | 4-MeS—$C_6H_4$ | 4-MeS—$C_6H_4$ | H | S | 8 | N—$C_7H_{15}$ | — |
| 425 | iPr | iPr | H | S | 8 | N—$C_7H_{15}$ | — |
| 426 | Ph | Ph | H | S | 8 | N—$(CH_2)_2OC_4H_9$ | — |
| 427 | 4-MeO—$C_6H_4$ | 4-MeO—$C_6H_4$ | H | S | 8 | N—$(CH_2)_2OC_4H_9$ | — |
| 428 | 4-$Me_2$N—$C_6H_4$ | 4-$Me_2$N—$C_6H_4$ | H | S | 8 | N—$(CH_2)_2OC_4H_9$ | — |
| 429 | 4-MeS—$C_6H_4$ | 4-MeS—$C_6H_4$ | H | S | 8 | N—$(CH_2)_2OC_4H_9$ | — |
| 430 | iPr | iPr | H | S | 8 | N—$(CH_2)_2OC_4H_9$ | — |
| 431 | Ph | Ph | H | S | 8 | N—$(CH_2)_2O$—$(CH_2)_2OCH_3$ | — |
| 432 | 4-MeO—$C_6H_4$ | 4-MeO—$C_6H_4$ | H | S | 8 | N—$(CH_2)_2O$—$(CH_2)_2OCH_3$ | — |
| 433 | 4-$Me_2$N—$C_6H_4$ | 4-$Me_2$N—$C_6H_4$ | H | S | 8 | N—$(CH_2)_2O$—$(CH_2)_2OCH_3$ | — |
| 434 | 4-MeS—$C_6H_4$ | 4-MeS—$C_6H_4$ | H | S | 8 | N—$(CH_2)_2O$—$(CH_2)_2OCH_3$ | — |
| 435 | iPr | iPr | H | S | 8 | N—$(CH_2)_2O$—$(CH_2)_2OCH_3$ | — |

TABLE 5-continued

Structure: R¹, R² on imidazole ring with N-R³, connected via X—(CH₂)$_{m+n+1}$—Y to purine-like ring system.

| Ex. | R¹ | R² | R³ | X | m + n + 1 | Y | m.p. |
|---|---|---|---|---|---|---|---|
| 436 | Ph | Ph | H | S | 8 | S | — |
| 437 | 4-MeO—C₆H₄ | 4-MeO—C₆H₄ | H | S | 8 | S | — |
| 438 | 4-Me₂N—C₆H₄ | 4-Me₂N—C₆H₄ | H | S | 8 | S | — |
| 439 | 4-MeS—C₆H₄ | 4-MeS—C₆H₄ | H | S | 8 | S | — |
| 440 | iPr | iPr | H | S | 8 | S | — |
| 441 | Ph | Ph | H | CH₂ | 5 | N—C₇H₁₅ | — |
| 442 | 4-MeO—C₆H₄ | 4-MeO—C₆H₄ | H | CH₂ | 5 | N—C₇H₁₅ | — |
| 443 | 4-Me₂N—C₆H₄ | 4-Me₂N—C₆H₄ | H | CH₂ | 5 | N—C₇H₁₅ | — |
| 444 | 4-MeS—C₆H₄ | 4-MeS—C₆H₄ | H | CH₂ | 5 | N—C₇H₁₅ | — |
| 445 | iPr | iPr | H | CH₂ | 5 | N—C₇H₁₅ | — |
| 446 | Ph | n-C₅H₁₁ | H | S | 5 | N—(CH₂)₂OC₄H₉ | — |
| 447 | 4-MeO—C₆H₄ | Ph | H | S | 5 | N—(CH₂)₂OC₄H₉ | — |
| 448 | 4-(C₂H₅)₂N—C₆H₄ | 4-(C₂H₅)₂N—C₆H₄ | H | S | 5 | N—(CH₂)₂OC₄H₉ | — |
| 449 | 4-Cl—C₆H₄ | 4-Cl—C₆H₄ | H | S | 5 | N—(CH₂)₂OC₄H₉ | — |
| 450 | 4-MeS—C₆H₄ | iPr | H | S | 5 | N—(CH₂)₂OC₄H₉ | — |
| 451 | Ph | Ph | CH₃ | NCH₃ | 5 | N—(CH₂)₂O—(CH₂)₂OCH₃ | — |
| 452 | 4-MeO—C₆H₄ | 4-MeO—C₆H₄ | CH₃ | NCH₃ | 5 | N—(CH₂)₂O—(CH₂)₂OCH₃ | — |
| 453 | 4-Me₂N—C₆H₄ | 4-Me₂N—C₆H₄ | CH₃ | NCH₃ | 5 | N—(CH₂)₂O—(CH₂)₂OCH₃ | — |
| 454 | 4-MeS—C₆H₄ | 4-MeS—C₆H₄ | CH₃ | NCH₃ | 5 | N—(CH₂)₂O—(CH₂)₂OCH₃ | — |
| 455 | iPr | iPr | CH₃ | NCH₃ | 5 | N—(CH₂)₂O—(CH₂)₂OCH₃ | — |
| 456 | Ph | Ph | H | SO₂ | 5 | SO₂ | — |
| 457 | 4-MeO—C₆H₄ | 4-MeO—C₆H₄ | H | SO₂ | 5 | SO₂ | — |
| 458 | 4-Me₂N—C₆H₄ | 4-Me₂N—C₆H₄ | H | SO₂ | 5 | SO₂ | — |
| 459 | 4-MeS—C₆H₄ | 4-MeS—C₆H₄ | H | SO₂ | 5 | SO₂ | — |
| 460 | iPr | iPr | H | SO₂ | 5 | SO₂ | — |

TABLE 6

Structure: R¹, R² on imidazole ring with N-R³, connected via X—(CH₂)$_m$—[phenylene]—(CH₂)$_n$—Y to purine ring.

| Ex. | R¹ | R² | R³ | X | m | ring | n | Y | m.p. |
|---|---|---|---|---|---|---|---|---|---|
| 461 | Ph | Ph | H | S | 1 | meta | 1 | N—C₇H₁₅ | — |
| 462 | 4-MeO—C₆H₄ | 4-MeO—C₆H₄ | H | S | 1 | meta | 1 | N—C₇H₁₅ | — |
| 463 | 4-Me₂N—C₆H₄ | 4-Me₂N—C₆H₄ | H | S | 1 | meta | 1 | N—C₇H₁₅ | — |
| 464 | 4-MeS—C₆H₄ | 4-MeS—C₆H₄ | H | S | 1 | meta | 1 | N—C₇H₁₅ | — |
| 465 | iPr | iPr | H | S | 1 | meta | 1 | N—C₇H₁₅ | — |
| 466 | Ph | Ph | H | S | 1 | meta | 1 | N—(CH₂)₂OC₄H₉ | — |
| 467 | 4-MeO—C₆H₄ | 4-MeO—C₆H₄ | H | S | 1 | meta | 1 | N—(CH₂)₂OC₄H₉ | — |
| 468 | 4-Me₂N—C₆H₄ | 4-Me₂N—C₆H₄ | H | S | 1 | meta | 1 | N—(CH₂)₂OC₄H₉ | — |
| 469 | 4-MeS—C₆H₄ | 4-MeS—C₆H₄ | H | S | 1 | meta | 1 | N—(CH₂)₂OC₄H₉ | — |
| 470 | iPr | iPr | H | S | 1 | meta | 1 | N—(CH₂)₂OC₄H₉ | — |
| 471 | Ph | Ph | H | S | 1 | meta | 1 | N—(CH₂)₂O—(CH₂)₂OCH₃ | — |
| 472 | 4-MeO—C₆H₄ | 4-MeO—C₆H₄ | H | S | 1 | meta | 1 | N—(CH₂)₂O—(CH₂)₂OCH₃ | — |
| 473 | 4-Me₂N—C₆H₄ | 4-Me₂N—C₆H₄ | H | S | 1 | meta | 1 | N—(CH₂)₂O—(CH₂)₂OCH₃ | — |
| 474 | 4-MeS—C₆H₄ | 4-MeS—C₆H₄ | H | S | 1 | meta | 1 | N—(CH₂)₂O—(CH₂)₂OCH₃ | — |
| 475 | iPr | iPr | H | S | 1 | meta | 1 | N—(CH₂)₂O—(CH₂)₂OCH₃ | — |
| 476 | Ph | Ph | H | S | 1 | meta | 1 | S | — |
| 477 | 4-MeO—C₆H₄ | 4-MeO—C₆H₄ | H | S | 1 | meta | 1 | S | 129–130 |
| 478 | 4-Me₂N—C₆H₄ | 4-Me₂N—C₆H₄ | H | S | 1 | meta | 1 | S | — |
| 479 | 4-MeS—C₆H₄ | 4-MeS—C₆H₄ | H | S | 1 | meta | 1 | S | — |
| 480 | iPr | iPr | H | S | 1 | meta | 1 | S | — |
| 481 | Ph | Ph | H | S | 1 | para | 1 | N—C₇H₁₅ | — |

TABLE 6-continued

| Ex. | R¹ | R² | R³ | X | m | ring | n | Y | m.p. |
|---|---|---|---|---|---|---|---|---|---|
| 482 | 4-MeO—C$_6$H$_4$ | 4-MeO—C$_6$H$_4$ | H | S | 1 | para | 1 | N—C$_7$H$_{15}$ | — |
| 483 | 4-Me$_2$N—C$_6$H$_4$ | 4-Me$_2$N—C$_6$H$_4$ | H | S | 1 | para | 1 | N—C$_7$H$_{15}$ | — |
| 484 | 4-MeS—C$_6$H$_4$ | 4-MeS—C$_6$H$_4$ | H | S | 1 | para | 1 | N—C$_7$H$_{15}$ | — |
| 485 | iPr | iPr | H | S | 1 | para | 1 | N—C$_7$H$_{15}$ | — |
| 486 | Ph | Ph | H | S | 1 | para | 1 | N—(CH$_2$)$_2$OC$_4$H$_9$ | — |
| 487 | 4-MeO—C$_6$H$_4$ | 4-MeO—C$_6$H$_4$ | H | S | 1 | para | 1 | N—(CH$_2$)$_2$OC$_4$H$_9$ | — |
| 488 | 4-Me$_2$N—C$_6$H$_4$ | 4-Me$_2$N—C$_6$H$_4$ | H | S | 1 | para | 1 | N—(CH$_2$)$_2$OC$_4$H$_9$ | — |
| 489 | 4-MeS—C$_6$H$_4$ | 4-MeS—C$_6$H$_4$ | H | S | 1 | para | 1 | N—(CH$_2$)$_2$OC$_4$H$_9$ | — |
| 490 | iPr | iPr | H | S | 1 | para | 1 | N—(CH$_2$)$_2$OC$_4$H$_9$ | — |
| 491 | Ph | Ph | H | S | 1 | para | 1 | N—(CH$_2$)$_2$O—(CH$_2$)$_2$OCH$_3$ | — |
| 492 | 4-MeO—C$_6$H$_4$ | 4-MeO—C$_6$H$_4$ | H | S | 1 | para | 1 | N—(CH$_2$)$_2$O—(CH$_2$)$_2$OCH$_3$ | — |
| 493 | 4-Me$_2$N—C$_6$H$_4$ | 4-Me$_2$N—C$_6$H$_4$ | H | S | 1 | para | 1 | N—(CH$_2$)$_2$O—(CH$_2$)$_2$OCH$_3$ | — |
| 494 | 4-MeS—C$_6$H$_4$ | 4-MeS—C$_6$H$_4$ | H | S | 1 | para | 1 | N—(CH$_2$)$_2$O—(CH$_2$)$_2$OCH$_3$ | — |
| 495 | iPr | iPr | H | S | 1 | para | 1 | N—(CH$_2$)$_2$O—(CH$_2$)$_2$OCH$_3$ | — |
| 496 | Ph | Ph | H | S | 1 | para | 1 | S | — |
| 497 | 4-MeO—C$_6$H$_4$ | 4-MeO—C$_6$H$_4$ | H | S | 1 | para | 1 | S | — |
| 498 | 4-Me$_2$N—C$_6$H$_4$ | 4-Me$_2$N—C$_6$H$_4$ | H | S | 1 | para | 1 | S | — |
| 499 | 4-MeS—C$_6$H$_4$ | 4-MeS—C$_6$H$_4$ | H | S | 1 | para | 1 | S | — |
| 500 | iPr | iPr | H | S | 1 | para | 1 | S | — |
| 501 | Ph | Ph | H | S | 1 | ortho | 1 | N—C$_7$H$_{15}$ | — |
| 502 | 4-MeO—C$_6$H$_4$ | 4-MeO—C$_6$H$_4$ | H | S | 1 | ortho | 1 | N—C$_7$H$_{15}$ | — |
| 503 | 4-Me$_2$N—C$_6$H$_4$ | 4-Me$_2$N—C$_6$H$_4$ | H | S | 1 | ortho | 1 | N—C$_7$H$_{15}$ | — |
| 504 | 4-MeS—C$_6$H$_4$ | 4-MeS—C$_6$H$_4$ | H | S | 1 | ortho | 1 | N—C$_7$H$_{15}$ | — |
| 505 | iPr | iPr | H | S | 1 | ortho | 1 | N—C$_7$H$_{15}$ | — |
| 506 | Ph | Ph | H | S | 1 | ortho | 1 | N—(CH$_2$)$_2$OC$_4$H$_9$ | — |
| 507 | 4-MeO—C$_6$H$_4$ | 4-MeO—C$_6$H$_4$ | H | S | 1 | ortho | 1 | N—(CH$_2$)$_2$OC$_4$H$_9$ | — |
| 508 | 4-Me$_2$N—C$_6$H$_4$ | 4-Me$_2$N—C$_6$H$_4$ | H | S | 1 | ortho | 1 | N—(CH$_2$)$_2$OC$_4$H$_9$ | — |
| 509 | 4-MeS—C$_6$H$_4$ | 4-MeS—C$_6$H$_4$ | H | S | 1 | ortho | 1 | N—(CH$_2$)$_2$OC$_4$H$_9$ | — |
| 510 | iPr | iPr | H | S | 1 | ortho | 1 | N—(CH$_2$)$_2$OC$_4$H$_9$ | — |
| 511 | Ph | Ph | H | S | 1 | ortho | 1 | N—(CH$_2$)$_2$O—(CH$_2$)$_2$OCH$_3$ | — |
| 512 | 4-MeO—C$_6$H$_4$ | 4-MeO—C$_6$H$_4$ | H | S | 1 | ortho | 1 | N—(CH$_2$)$_2$O—(CH$_2$)$_2$OCH$_3$ | — |
| 513 | 4-Me$_2$N—C$_6$H$_4$ | 4-Me$_2$N—C$_6$H$_4$ | H | S | 1 | ortho | 1 | N—(CH$_2$)$_2$O—(CH$_2$)$_2$OCH$_3$ | — |
| 514 | 4-MeS—C$_6$H$_4$ | 4-MeS—C$_6$H$_4$ | H | S | 1 | ortho | 1 | N—(CH$_2$)$_2$O—(CH$_2$)$_2$OCH$_3$ | — |
| 515 | iPr | iPr | H | S | 1 | ortho | 1 | N—(CH$_2$)$_2$O—(CH$_2$)$_2$OCH$_3$ | — |
| 516 | Ph | Ph | H | S | 1 | ortho | 1 | S | — |
| 517 | 4-MeO—C$_6$H$_4$ | 4-MeO—C$_6$H$_4$ | H | S | 1 | ortho | 1 | S | — |
| 518 | 4-Me$_2$N—C$_6$H$_4$ | 4-Me$_2$N—C$_6$H$_4$ | H | S | 1 | ortho | 1 | S | — |
| 519 | 4-MeS—C$_6$H$_4$ | 4-MeS—C$_6$H$_4$ | H | S | 1 | ortho | 1 | S | — |
| 520 | iPr | iPr | H | S | 1 | ortho | 1 | S | — |
| 521 | Ph | Ph | H | CH$_2$ | 1 | para | 1 | N—C$_7$H$_{15}$ | — |
| 522 | 4-MeO—C$_6$H$_4$ | 4-MeO—C$_6$H$_4$ | H | CH$_2$ | 1 | para | 1 | N—C$_7$H$_{15}$ | — |
| 523 | 4-Me$_2$N—C$_6$H$_4$ | 4-Me$_2$N—C$_6$H$_4$ | H | CH$_2$ | 1 | para | 1 | N—C$_7$H$_{15}$ | — |
| 524 | 4-MeS—C$_6$H$_4$ | 4-MeS—C$_6$H$_4$ | H | CH$_2$ | 1 | para | 1 | N—C$_7$H$_{15}$ | — |
| 525 | iPr | iPr | H | CH$_2$ | 1 | para | 1 | N—C$_7$H$_{15}$ | — |
| 526 | Ph | n-C$_5$H$_{11}$ | H | S | 1 | para | 2 | N—(CH$_2$)$_2$OC$_4$H$_9$ | — |
| 527 | 4-MeO—C$_6$H$_4$ | Ph | H | S | 1 | para | 2 | N—(CH$_2$)$_2$OC$_4$H$_9$ | — |
| 528 | 4-(C$_2$H$_5$)$_2$N—C$_6$H$_4$ | 4-(C$_2$H$_5$)$_2$N—C$_6$H$_4$ | H | S | 1 | para | 2 | N—(CH$_2$)$_2$OC$_4$H$_9$ | — |
| 529 | 4-Cl—C$_6$H$_4$ | 4-Cl—C$_6$H$_4$ | H | S | 1 | para | 2 | N—(CH$_2$)$_2$OC$_4$H$_9$ | — |
| 530 | 4-MeS—C$_6$H$_4$ | iPr | H | S | 1 | para | 2 | N—(CH$_2$)$_2$OC$_4$H$_9$ | — |
| 531 | Ph | Ph | CH$_3$ | NMe | 2 | para | 1 | N—(CH$_2$)$_2$O—(CH$_2$)$_2$OCH$_3$ | — |
| 532 | 4-MeO—C$_6$H$_4$ | 4-MeO—C$_6$H$_4$ | CH$_3$ | NMe | 2 | para | 1 | N—(CH$_2$)$_2$O—(CH$_2$)$_2$OCH$_3$ | — |
| 533 | 4-Me$_2$N—C$_6$H$_4$ | 4-Me$_2$N—C$_6$H$_4$ | CH$_3$ | NMe | 2 | para | 1 | N—(CH$_2$)$_2$O— | |

TABLE 6-continued

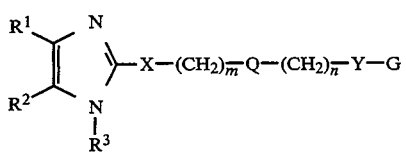

| Ex. | R¹ | R² | R³ | X | m | ring | n | Y | m.p. |
|---|---|---|---|---|---|---|---|---|---|
| 534 | 4-MeS—C₆H₄ | 4-MeS—C₆H₄ | CH₃ | NMe | 2 | para | 1 | (CH₂)₂OCH₃<br>N—(CH₂)₂O—<br>(CH₂)₂OCH₃ | — |
| 535 | iPr | iPr | CH₃ | NMe | 2 | para | 1 | N—(CH₂)₂O—<br>(CH₂)₂OCH₃ | — |
| 536 | Ph | Ph | H | SO₂ | 1 | para | 1 | SO₂ | — |
| 537 | 4-MeO—C₆H₄ | 4-MeO—C₆H₄ | H | SO₂ | 1 | para | 1 | SO₂ | — |
| 538 | 4-Me₂N—C₆H₄ | 4-Me₂N—C₆H₄ | H | SO₂ | 1 | para | 1 | SO₂ | — |
| 539 | 4-MeS—C₆H₄ | 4-MeS—C₆H₄ | H | SO₂ | 1 | para | 1 | SO₂ | — |
| 540 | iPr | iPr | H | SO₂ | 1 | para | 1 | SO₂ | — |

What is claimed is:

1. A compound of Formula (I):

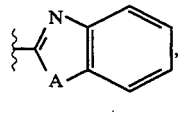

(I)

and stereoisomers and pharmaceutically acceptable salts thereof, wherein:

X and Y are selected independently from the groups $S(O)_p$, $CH_2$, or $NR^4$;

Q is selected from either $CH_2$, or an aromatic ring selected from the group consisting of benzene, pyrrole, furan, or thiophene, said aromatic ring being connected through two ring substitution sites and said aromatic ring being optionally substituted with 1-3 groups independently selected from F, Cl, Br, OH, $C_1$-$C_4$ alkoxy, $C_1$-$C_4$ alkyl, $C_3$-$C_8$ branched alkyl, $S(O)_t(C_1$-$C_6$ alkyl), $NO_2$, $CF_3$, or $NR^{15}R^{16}$;

G is selected from the groups

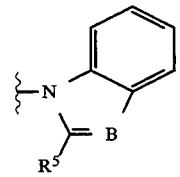

each being optionally substituted at valence-allowed sites with 1-3 groups independently selected from F, Cl, Br, OH, $C_1$-$C_4$ alkoxy, $C_1$-$C_4$ alkyl, $C_3C_8$ branched alkyl, $S(O)_t(C^1$-$C_6$ alkyl), $NO_2$, $CF_3$, or $NR^{15}R^{16}$;

wherein A is O, or NH, and B is independently CH or N;

R¹ and R² are selected independently from H, $C_1$-$C_8$ alkyl, $C_3$-$C_8$ branched alkyl, $C_3$-$C_7$ cycloalkyl, $C_4$-$C_{10}$ cycloalkylalkyl, $C_7$-$C_{14}$ aralkyl, pyridyl, thienyl, furanyl, or phenyl; each being optionally substituted with 1-3 groups independently selected from F, Cl, Br, OH, $C_1$-$C_4$ alkoxy, $C_1C_4$ alkyl, $C_3$-$C_8$ branched alkyl, $S(O)_t(C_1$-$C_6$ alkyl), $NO_2$, $CF_3$, or $NR^{15}R^{16}$;

R³ is H, $C_1$-$C_6$ alkyl, allyl, benzyl, or phenyl; each being optionally substituted with F, Cl, $CH_3$, $OCH_3$, or $CF_3$;

R⁴ is H, $C_1$-$C_8$ alkyl, $C_3$-$C_{10}$ alkoxyalkyl, $C_5$-$C_{12}$(alkoxy)alkoxyalkyl, $C_3$-$C_8$ branched alkyl, $C_{7-C14}$ phenylalkyl, or phenyl, each being optionally substituted with 1-3 groups selected from $C_1$-$C_4$ alkyl, $C_1$-$C_4$ alkoxy, $C_2$-$C_8$ dialkylamino, $C_1$-$C_4$ alkylthio, halogen, or $NO_2$;

R¹⁵ and R¹⁶ are selected independently from H, $C_1$-$C_8$ alkyl, benzyl, or phenyl;

m and n are independently 0-6, and selected so that the total number of $CH_2$ groups in the chain between X and G is at least 2; and p and t are independently 0-2.

2. A compound of claim 1, stereoisomers and pharmaceutically acceptable salts thereof, wherein:

X and Y are independently $S(O)_p$ or $NR^4$;

Q is selected from either $CH_2$, or an aromatic ring selected from the group consisting of benzene, pyrrole, furan or thiophene, said aromatic ring being connected through two ring substitution sites and said aromatic ring being optionally substituted with a 1-3 groups independently selected from $C_1$-$C_4$ alkyl, $C_1$14 $C_4$ alkoxy, $C_2$-$C_8$ dialkylamino, $C_1$-$C_4$ alkylthio, halogen or $NO_2$;

G is selected from the groups

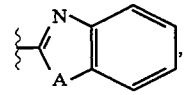

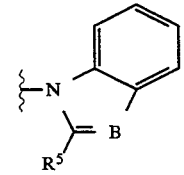

each being optionally substituted at valence-allowed sites with 1-3 groups independently selected from $C_1$-$C_4$ alkyl, $C_1$-$C_4$ alkoxy, $C_2$-$C_8$ dialkylamino, $C_1$-$C_4$ alkylthio, halogen, or $NO_2$;

wherein A is O, or NH, and B is independently CH or N;

R$^1$ and R$^2$ are selected independently from H, C$_1$-C$_4$ alkyl, C$_3$-C$_8$ branched alkyl, C$_3$-C$_7$ cycloalkyl, or phenyl, each being optionally substituted with 1-3 groups selected from Cl, C$_1$-C$_4$ alkyl, C$_1$-C$_4$ alkoxy, C$_2$-C$_8$ dialkylamino, or C$_1$-C$_4$ alkylthio;

R$^3$ is H;

R$^4$ is H, C$_1$-C$_8$ alkyl, C$_3$-C$_{10}$ alkoxyalkyl, C$_5$-C$_{12}$(alkoxy)alkoxyalkyl, C$_3$-C$_8$ branched alkyl, C$_7$-C$_{14}$ phenylalkyl, or phenyl, each being optionally substituted with 1-3 groups selected from C$_1$-C$_4$ alkyl, C$_1$-C$_4$ alkoxy, C$_2$-C$_8$ dialkylamino, C$_1$-C$_4$ alkylthio, halogen, or NO$_2$;

m and n are independently 0-6, and selected so that the total number of CH$_2$ groups in the chain between X and G is at least 2; and p is 0-2;

R$^5$ is H, C$_1$-C$_4$ alkyl, C$_3$-C$_7$ branched alkyl, C$_1$-C$_4$ alkoxy, C$_1$-C$_4$ alkylthio, or NR$^6$R$^7$;

R$^6$ and R$^7$ are independently selected from the groups H, C$_1$-C$_4$ alkyl, or phenyl.

3. A compound of claim 1, stereoisomers and pharmaceutically acceptable salts thereof, wherein:

X and Y are independently S(O)$_p$ or NR$^4$;

Q is selected from either CH$_2$, benzene, furan or thiophene, wherein the benzene, furan, or thiophene are unsubstituted except for the connection through two ring substitution sites;

G is selected from the groups

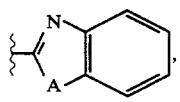

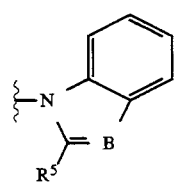

each being optionally substituted at valence-allowed sites with 1-3 groups independently selected from C$_1$-C$_4$ alkyl, C$_1$-C$_4$ alkoxy, C$_2$-C$_8$ dialkylamino, C$_1$-C$_4$ alkylthio, halogen or NO$_2$;

wherein A is O, or NH, and B is independently CH or N;

R$^1$ and R$^2$ are selected independently from C$_3$-C$_8$ branched alkyl, C$_3$-C$_7$ cycloalkyl, or phenyl, phenyl being optionally substituted with one of CH$_3$O, (CH$_3$)$_2$N, or CH$_3$S;

R$^3$ is H;

R$^4$ is C$_1$-C$_8$ alkyl, C$_3$-C$_{10}$ alkoxyalkyl, C$_5$-C$_{12}$(alkoxy)alkoxyalkyl, C$_3$-C$_8$ branched alkyl, or phenyl;

m is 1-3;

n is 0-3;

p is 0;

R$^5$ is H, C$_1$-C$_4$ alkyl, C$_3$-C$_7$ branched alkyl, C$_1$-C$_4$ alkoxy, C$_1$-C$_4$ alkylthio, or NR$^6$R$^7$;

R$^6$ and R$^7$ are independently selected from the groups H, C$_1$-C$_4$ alkyl, or phenyl.

4. A compound of claim 1, stereoisomers and pharmaceutically acceptable salts thereof, selected from the group consisting of:

2-[5-(N-(1H-benzoxazol-2-yl)-N-heptylamino)pentyl]thio-4,5-diphenyl-1H-imidazole;

4,5-bis(4-methoxyphenyl)-2-[5-(N-(1H-benzoxazol-2-yl)-N-heptylamino)-pentyl]thio-1H-imidazole;

4,5-bis(4-methoxyphenyl)-2-[5-(N-(1H-benzimidazol-2-yl)-N-heptylamino)-pentyl]thio-1H-imidazole;

4,5-bis(4-dimethylaminophenyl)-2-[5-(2-(1methylethyl)-1H-benzimidazol-1-yl)pentyl]thio-1-H-imidazole.

5. A pharmaceutical composition comprising an effective ACAT-inhibiting or antiartherosclerotic amount of a compound of claim 1 and a pharmaceutically acceptable carrier.

6. A pharmaceutical composition comprising an effective ACAT-inhibiting or antiartherosclerotic amount of a compound of claim 2 and a pharmaceutically acceptable carrier.

7. A pharmaceutical composition comprising an effective ACAT-inhibiting or antiartherosclerotic amount of a compound of claim 3 and a pharmaceutically acceptable carrier.

8. A pharmaceutical composition comprising an effective ACAT-inhibiting or antiartherosclerotic amount of a compound of claim 4 and a pharmaceutically acceptable carrier.

9. A method of treating hypercholesterolemia or artherosclerosis in a mammal comprising administering to the mammal a therapeutically effective amount of a composition of claim 1.

10. A method of treating hypercholesterolemia or artherosclerosis in a mammal comprising administering to the mammal a therapeutically effective amount of a composition of claim 2.

11. A method of treating hypercholesterolemia or artherosclerosis in a mammal comprising administering to the mammal a therapeutically effective amount of a composition of claim 3.

12. A method of treating hypercholesterolemia or artherosclerosis in a mammal comprising administering to the mammal a therapeutically effective amount of a composition of claim 4.

13. The compound of claim 2 which is:

2-[5-(N-1H-benzoxazol-2-yl)-N-heptylamino)pentyl]thio-4-5-diphenyl-1H-imidazole; or stereoisomers and pharmaceutically acceptable salts thereof.

* * * * *